United States Patent [19]

Ogura et al.

[11] Patent Number: 4,695,833
[45] Date of Patent: Sep. 22, 1987

[54] MAN-MACHINE INTERFACE TYPE PORTABLE ULTRASONIC COMPOSITE MEASURING APPARATUS

[75] Inventors: Yukio Ogura, Amimachi; Seiji Nasu, Hitachi, both of Japan

[73] Assignees: Hitachi Construction Machinery Co., Tokyo; Hitachi Engineering Co., Ltd., Ibaraki, both of Japan

[21] Appl. No.: 673,704

[22] PCT Filed: Mar. 28, 1983

[86] PCT No.: PCT/JP83/00094
 § 371 Date: Nov. 13, 1984
 § 102(e) Date: Nov. 13, 1984

[87] PCT Pub. No.: WO84/03944
 PCT Pub. Date: Oct. 11, 1984

[51] Int. Cl.⁴ .............................................. G09G 1/00
[52] U.S. Cl. .................................... 340/722; 340/706; 340/709; 340/720; 324/121 R
[58] Field of Search ............... 340/706, 712, 715, 720, 340/722; 324/121 R

[56] References Cited

U.S. PATENT DOCUMENTS

| | | | |
|---|---|---|---|
| 4,386,232 | 5/1983 | Slater | 340/712 |
| 4,396,977 | 8/1983 | Slater et al. | 340/706 |
| 4,432,235 | 2/1984 | Renzel et al. | 340/715 |
| 4,476,463 | 10/1984 | Ng et al. | 340/712 |
| 4,479,197 | 10/1984 | Haag et al. | 340/712 |
| 4,555,699 | 11/1985 | Citron et al. | 340/706 |
| 4,578,640 | 3/1986 | Crooke et al. | 324/121 R |

Primary Examiner—Gerald L. Brigance
Assistant Examiner—Jeffery A. Brier
Attorney, Agent, or Firm—Wenderoth, Lind & Ponack

[57] ABSTRACT

A man-machine interface type portable ultrasonic composite measuring apparatus includes an oscilloscope, a position-detecting panel mounted on the display surface of the oscilloscope, a keyboard for effecting a man-machine interface, and a computer which introduces position signals detected from the panel and contents designated by the keyboard. The waveforms to be observed include all objects to be measured, that can be observed in the form of electric signals and that form optimum ultrasonic echos. A position-detecting panel is constructed in the form of a touch panel.

1 Claim, 37 Drawing Figures

FIG. 12(A)
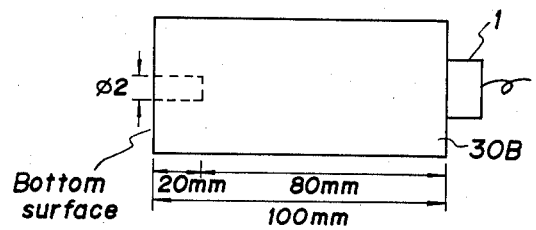
FIG. 12(B)
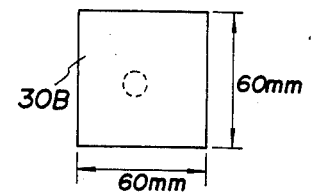
FIG. 12(C)
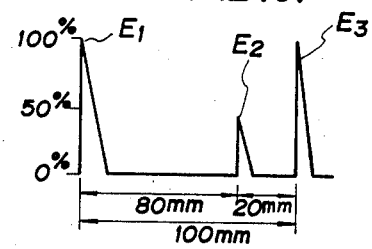
FIG. 13
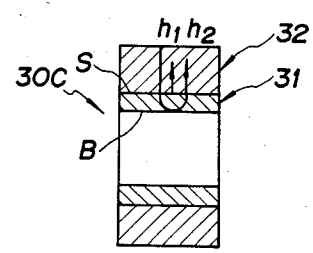
FIG. 14(A)    FIG. 14(B)    FIG. 14(C)
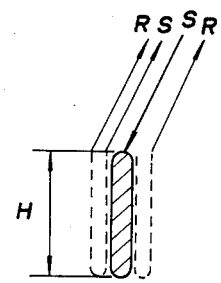 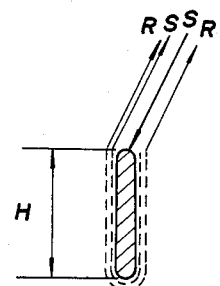 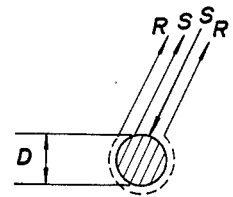

MAN-MACHINE INTERFACE TYPE PORTABLE ULTRASONIC COMPOSITE MEASURING APPARATUS

FIELD OF THE INVENTION

The present invention relates to a measuring apparatus which measures observation waveforms of an object to be measured using an oscilloscope device.

The object includes a field of non-destructive inspection utilizing ultrasonic waves. An ultrasonic transducer emits ultrasonic waves into a material to be inspected, and waves reflected by the material are introduced as observation waveforms via the transducer and are displayed on the cathode-ray tube. The observation waveforms change extensively depending upon the material to be inspected, the shape thereof, and the items of inspection.

In measuring the objects inclusive of non-destructive inspection of a material by the ultrasonic waves, how to observe the observation waveforms casts an important theme. Observation of the waveforms can be divided into an observation method of observing the waveforms by eye, and an automatic observation method of automatically monitoring the waveforms.

BACKGROUND OF THE ART

The oscilloscope device introduces a variety of observation signals from an external object that is to be measured, and displays the observation waveforms representing the observation signals on the picture plane of a cathode-ray tube CRT. When it is desired to measure a particular position in the observation waveforms by using the oscilloscope device, the operator observes it using his eyes.

However, measurement based upon the use of ones eyes involves errors, and requires a period of time that cannot be neglected. In particular, when complex waveforms are displayed on the cathode-ray tube, measuring error increases and measuring time increases, too.

There has been proposed a method of obtaining the measurement completely automatically to substitute for the measurement by the operator based upon the oscilloscope device. Namely, this method makes use of an automatic measuring device which consists of an A/D converter and a microcomputer, arranged in parallel with the oscilloscope device. The A/D converter samples the observation signals and subjects them to the A/D conversion. The microcomputer introduces digital outputs from the A/D converter, selects necessary values of observation, and collects the selected values of observation.

The above method is effective when the observation signals have regularity or when the observation signals of a low speed are to be treated. However, it becomes difficult to perform the automatic measurement when the observation signals of high speeds are to be treated or when the observation signals undergo the change in a very complex manner.

Another method consists of introducing A/D outputs of observation signals in real time, and then selecting the measured values in off-line. However, when complex observation signals are to be treated, it becomes necessary to provide a memory for filing the data that are introduced in real time, i.e., to provide a memory having a large capacity. If it is attempted to introduce and to treat the data in real time, then the computer must bear a large burden.

On the other hand, the data required for the subsequent arithmetic operation do not represent all of the input signals even when the input signals are automatically introduced or even when an operator visually reads the data on the oscilloscope. They form numerical points on the input signals. To find the data (effective data) of numerical points required for the arithmetic operation, makes a problem of software for the operator or for the computer. In the case of the computer, the software technique makes it possible to sufficiently cope with the problem when the content of data after A/D converted is as simple as to distinguish whether the level of input signals is greater than a reference value or not, or when the presence of signals having a level greater than a given level is to be confirmed, or when the input time of the signals is to be calculated, even when the input signals have a level that does not change or that changes vigorously. Often, however, the input signals may change vigorously, or the portions that serve as effective data may vary depending upon the change of signals. In this case, the content of data processing changes depending upon the measuring conditions or depending upon the change of input wave forms, and it is not easy to develop a software by taking these various changes into consideration.

Complex vibration signals include response signals from the flaw detection using ultrasonic waves and detection signals from a transducer. In the flaw detection using ultrasonic waves, various materials having various construction will be inspected, and the flaw detection can be carried out in a variety of manners. Furthermore, the observation values to be measured varies depending upon the content. The same also holds true when the surface pressure is measured by the ultrasonic waves.

According to a conventional technique, a panel for detecting the position is mounted on the front surface of the cathode-ray tube, and the panel for detecting the position (touch sensor) is used for the same purpose as a light pen. A variety of predetermined characters or symbols to be fed to the computer are displayed on the cathode-ray tube at predetermined positions, and the characters or simbols are designated by the panel for detecting the positions. Coordinate signals corresponding to the designated characters are taken out to find the characters or symbols corresponding to the coordinate signals, and the characters or symbols are input to the computer (refer to Japanese Laid-Open Patent. No. 19836/1982).

The above method makes use of the panel for detecting positions instead of the light pen, and what are displayed on the cathode-ray tube are limited to characters or figures. However, the above method is not applicable to observing the waveforms since the positions of observation waveforms have not been specified beforehand on the cathode-ray tube.

U.S. Pat. No. 3,608,361 discloses such conventional apparatus wherein the observation response signals from the ultrasonic transducer are displayed on the CRT to read out the position and size of the observation waveforms. In this apparatus, there is provided a scaled sheet on the CRT displaying surface. The position and size of the observation waveforms behind the sheet are measured by reading the scale of the scaled sheet. When measuring, it is necessary for the operator to read the scale using his eyes. Furthermore, a variety of scaled sheets must be prepared beforehand in accordance with different kinds of objects to be observed. It is easily understood from the above example that the observation of ultrasonic waveforms is more troublesome than that of the general observation waveforms.

The objects of the present invention is to provide an interface type portable ultrasonic composite measuring apparatus which is capable of variety of ultrasonic measuring in accordance with a plurality of measuring modes.

Another object of the present invention is to provide a man-made interface type portable ultrasonic composite measuring apparatus in which semiautomatic detection of a variety of observation waveforms are carried out in accordance with a plurality of measuring modes and automatic processing after the detection in accordance with the measuring modes.

A further object of the present invention is to provide a man-machine interface type portable ultrasonic measuring apparatus in which variety of processing programs are given to a microcomputer in accordance with the measuring modes, and is capable of reading the observation waveforms according to man-machine processing for each of the processing programs.

Another object of the present invention is to provide a man-machine interface type portable ultrasonic composite measuring apparatus which is formed in a hand-held fashion.

According to the present invention, a plurality of the processing programs (software) are given to the microcomputer in accordance with the composite measuring modes, and a certain mode is selected from among the composite measuring modes by a keyboard, and in accordance with the selected processing mode, coordinate values of the observation waveforms are read out by the man-machine interface. Furthermore, a position detecting panel of transparent material is mounted in front of the displaying surface of the oscilloscope device for reading the observation waveforms. Designation of the observation waveforms is carried out via the transparent panel and the coordinate values designated are automatically input to a microcomputer to carry out the necessary processing.

Here, the position-detecting panel is thin, flat and transparent. When a given point is depressed, the panel produces a signal that indicates the depressed point. This signal is produced as X-coordinate and Y-coordinate signals.

The computer has various processing programs for man-machine use. X- and Y-coordinate signals are inputted to the microcomputer. The computer further stores in the memory X- and Y-coordinate signals corresponding to the depressed point on the position-detecting panel as measured values.

According to the present invention, furthermore, a display unit is provided in addition to the oscilloscope device. The display unit is provided for man-machine use, and gives operation instructions to the operator in accordance with the instructions from the computer. The operator performs the operation in compliance with the operation instruction. The display unit further numerically displays the results of arithmetic operations based upon the X- and Y-coordinate data that have been measured. The oscilloscope device is to display the observation waveforms, but cannot directly communicate with the computer. The display unit realizes the direct communication with the computer on behalf of the oscilloscope.

The present invention further has input means which transmits the will of the operator to the computer. Usually, the input means consists of a keyboard. The input means gives instructions for effecting the operation, and inputs necessary set values.

The present invention further has a printer which is helpful for recording the steps of the operation and for checking the steps of the operation.

BRIEF DESCRIPTION OF THE DRAWINGS

FIGS. 12(A), 12(B) and 12(C) are diagrams illustrating the calibration;

FIG. 13 is a diagram illustrating the measurement of surface pressure;

FIGS. 14(A), 14(B) and 14(C) are diagrams illustrating the flaw detection;

DESCRIPTION OF THE PREFERRED EMBODIMENT

Figure 1:
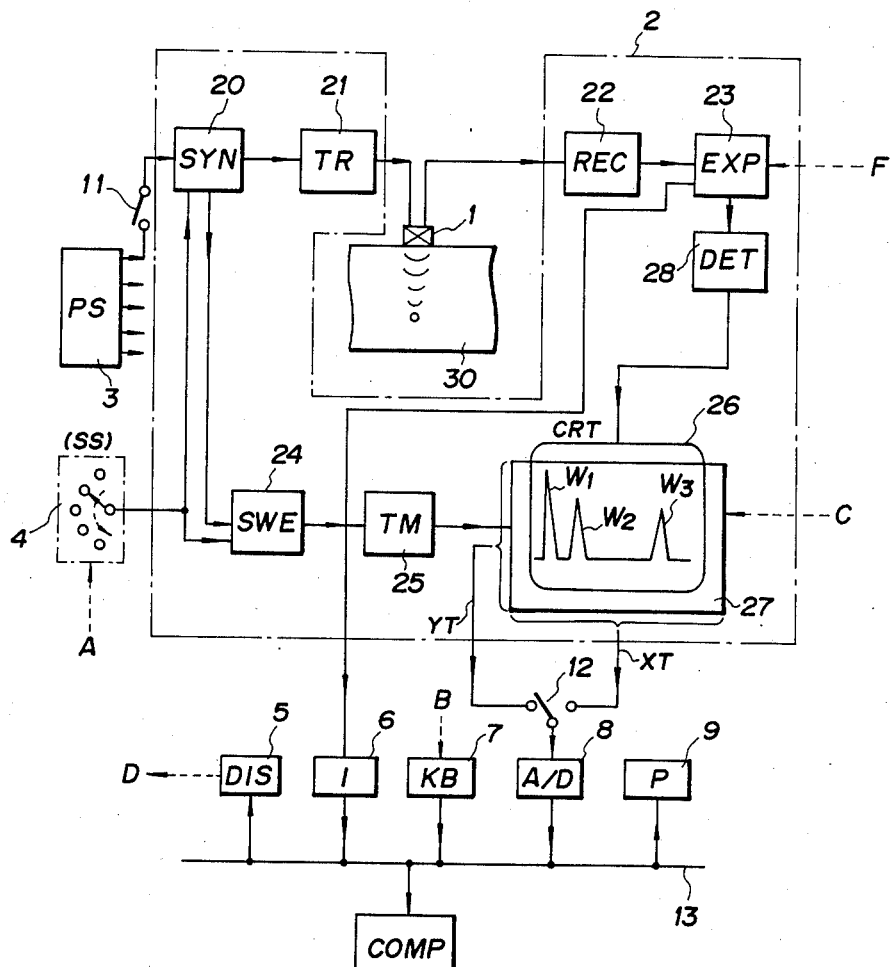
FIG. 1 is a diagram of a measuring apparatus according to an embodiment of the present invention.

FIG. 1 is a diagram of an ultrasonic composite measuring apparatus of the man-machine type according to an embodiment of the present invention. Solid lines indicate signal lines in the machine system, and dotted lines indicate an operation system (including monitoring system) in the man system.

The composite measurement is to effect two kinds of measurements, i.e., to effect the flaw detection and the measurement of surface pressure, where the flaw detection has at least six modes for measuring flaws, and the measurement is carried out according to the six measuring modes.

Measurement according to the six flaw measuring modes include;

(1) Measurement by the method of a maximum echo height;
(2) Measurement by the method of correcting the probe distance;
(3) Measurement by the surface-wave method of mode conversion;
(4) Measurement by the 6-dB drop method;

(5) Measurement by the method of scattered longitudinal waves; and (6) Measurement by the method of peak echo at an end portion.

A transducer 1 emits ultrasonic waves into a material 30 that is to be inspected, and detects the waves reflected by the material 30.

An oscilloscope device 2 consists of a synchronizing circuit SYN 20, a transmitter circuit TR 21, a receiver circuit REC 22, a logarithm converter EXP 23, a detector DET 28, a sweeping circuit SWE 24, a time base portion TM 25, a cathode-ray tube CRT 26, and a position-detecting panel 27.

Outside the oscilloscope device 2, provision is made of a power source PS 3, a repetitive period setter SS 4, a liquid crystal display DIS 5, an input unit I 6, a keyboard KB 7, an A/D converter AD 8, a printer P 9, a microcomputer COMP 10, switches 11, 12, and a common bus 13.

The synchronizing circuit 20 generates a signal voltage that restricts the time of the circuits in the oscilloscope device 2. The synchronizing circuit 20 is started by the application of a voltage from the power source 3 via the switch 11. The period of synchronism can be changed depending upon the setpoint value of the repetitive period setter 4.

Upon receipt of a signal voltage from the synchronizing circuit 20, the transmitter circuit 21 generates a start pulse to the transducer 1. Upon receipt of the start pulse, the ultrasonic transducer 1 oscillates specific ultrasonic pulses that transmit to the interior of the material 30 to be inspected. If there exists any flaw, the waves are reflected by the flaw. The transducer 1 receives the reflected waves and generates an electric signal corresponding to the intensity of the reflected waves.

The receiver circuit 22 consists of an amplifier which receives and amplifies a signal that is sent from the transducer 1 and that corresponds to a reflected wave. The logarithmic converter 23 receives the output amplified by the receiver circuit 22 and effects the logarithm conversion. Therefore, signals are obtained in the form of decibel display. The detector 28 rectifies high-frequency outputs from the logarithmic converter 23 to obtain a signal in the form of a DC voltage, such that the instruction system relative to the cathode-ray tube is converted in the half-swing instruction which is called the DC system. The detector 28 further works to remove noise components.

The sweeping circuit 24 synchronizes the time for generating a triangular wave on a time basis (corresponds to the abscissa on the display picture plane of cathode-ray tube) based upon a synchronizing signal from the synchronizing circuit 20. The sweeping circuit 24 is also used for displaying the vicinity of measuring point on the cathode-ray tube, and for bringing the origin of beam path at the time of tilted incidence into agreement with the zero point on the graduated plate. The time axis portion 25 produces a voltage for moving a bright point at an equal speed in the horizontal direction on the display picture plane of cathode-ray tube.

The cathode-ray tube 26 receives a time axis signal of the time base portion 25 and a detect output of the detector 28, and displays the detect output on the time base. Among the waveforms displayed on the cathode-ray tube 26, W1 denotes a transmitted wave signal, and W2 and W3 denote reflected wave signals. The transmitted wave signal W1 is produced at the time of emitting ultrasonic waves, and is received by the receiver circuit 22 via the transducer 1. The reflected wave signals W2, W3 are those reflected by the material 30 to be inspected, and are received by the receiver circuit 22 via the vibrator 1 as mentioned earlier.

The position-detecting panel 27 is made of a transparent material, and is mounted on the display picture plane of the cathode-ray tube 26. The position-detecting panel 27 works as a touch sensor which, when the operator depresses a given position by a pointer (not shown) or by hand, generates a signal that represents the X-coordinate of the depressed position from a terminal XT and generates a signal that represents the Y-coordinate from a terminal YT.

The coordinate position on the display picture plane of the cathode-ray tube is read by the position-detecting panel 27. Since the detecting panel 27 is transparent, the instruction of position of the detecting panel 27 also serves as the instruction of position on the display picture plane of the cathode-ray tube. If the coordinate axes of the detecting panel 27 are brought into agreement with the coordinate axes of the display picture plane, the signals of the detecting panel 27 through the terminals XT, YT represent the coordinate of the instructed position on the display picture plane of the cathode-ray tube. When the coordinate axes of the detecting panel 27 are not in agreement with the coordinate axes on the display picture plane, the equations for conversion calculations of the two coordinate systems should be prepared in the microcomputer 10, and the signals from the terminals XT, YT should be sent into the microcomputer 10 to convert them into coordinates on the display picture plane of the cathode-ray tube according to the equations for conversion calculations.

The position on the display picture plane of the cathode-ray tube to be read by the position-detecting panel 27, is a particular position among the received wave signals W1, W2, W3, and is just the waveform data of the received wave signal. Representative examples include maximum amplitudes of the waveforms W1, W2 and W3, and include times until W2 and W3 rise with the rise of the waveform W1 as a reference. The maximum amplitudes and the time between the transmitted wave and the reflected wave, are indispensable for the analysis of reflected waves. The waveform data indispensable for the analysis of reflected waves are detected by the position-detecting panel 27 relying upon the man-machine operation.

Owing to the man-machine operation, furthermore, a required position can be instructed freely and correctly, and can be input, irrespective of the display waveform.

According to a conventional art, use is made of the position-detecting panel instead of a light pen. The position-detecting panel is mounted in front of the display picture plane which displays a plurality of predetermined characters or symbols at specified positions. Positions of the characters to be selected on the display picture plane are input using the position-detecting panel. Based upon the positions of the position-detecting panel, processing is effected to specify the characters that are now being displayed and that are selected. The thus specified character are input to the microcomputer.

According to the present invention, the position-detecting panel works to detect the waveform data. Therefore, there is no need of effecting the processing to specify the characters, unlike the conventional art. Furthermore, the contents displayed on the cathode-ray tube according to the present invention are observation waveforms from the object that is to be measured. In the conventional art, the displayed contents are not observation waveforms but are characters prepared off-line. Furthermore, the present invention offers an analog display, whereas the conventional example offers a digital display.

The common bus 13 is controlled by the microcomputer 10. The display unit 5, input unit 6, keyboard 7, A/D converter 8 and printer 9 are also controlled by the microcomputer 10.

The microcomputer 10 stores in the ROM thereof the processing program for composite measurement. These processing programs are used for processing specified information consisting of a measurement procedure, a measurement object and a measurement position in accordance with a read-out processing program. These specified informations are sent to the display unit to be displayed thereon as the operation indicative informations for the operator. The operation of these processing programs and the display units will be described hereinafter. The processing program for composite measurement covers a processing program for surface pressure measurement, and a processing program for flaw detection. Furthermore, the processing program for flaw detection has six operation modes as described earlier.

The processing program for surface pressure measurement and the processing program for flaw detection are accessed by the two modes. The first mode is a calibration mode, and the second mode is an operation mode. The calibration mode is a preparatory operation using a standard test block prior to effecting the measurement, and is used for calibrating a variety of data. The operation mode stands for the operation during the practical measurement. In measuring the surface pressure, for instance, the processing program for surface pressure measurement is started by the calibration mode, and the surface pressure relative to the standard test piece is measured as instructed by the program, thereby to obtain a standard data. Then, the operation mode is entered. Namely, the processing program for surface pressure measurement is started, and the surface pressure relative to the material to be inspected is measured as instructed by the program, thereby to obtain a measured data.

The processing program for flaw detection is also started during both the calibration and the measurement, when the flaw detection is being carried out. The calibrated data is obtained during the calibration, and the measured data is obtained during the measurement.

The processing programs for surface pressure and flaw detection are started by the keyboard 7.

The calibrated data and measured data are obtained by the man-machine system. Namely, the individual programs give instruction of operation on the liquid crystal display unit during the steps of processing. The operator performs the operation according to the instruction of operation. During the operation, the operator reads and designates the waveform data that are displayed using the position-detecting panel 27. The read results are input to the microcomputer 10 via the switch 12 and the A/D converter 8. As the data are input, the microcomputer 10 stores them in the memory, and further sends them to the liquid crystal display unit 5 to display them.

The content of operation of one measuring item, usually, consists of a plurality of operation instructions. The processing by the man-machine system is carried out for every instruction of operation.

The input unit 6 receives a gain setpoint value of the logarithmic converter 23, and sends it to the microcomputer 10. The liquid crystal display unit 5 plays an important role when the operator executes the man-machine interface. In particular, the oscilloscope device 2 displays only the observation waveforms from the object that is to be measured. The contents of instruction related to operation items by the microcomputer 10, are not displayed on the oscilloscope device 2. Since the contents of instructions related to operation items are not displayed on the oscilloscope device 2, there is provided a liquid crystal display unit 5 to instruct operation items.

In addition to instructing the operation items, the liquid crystal display unit 5 displays the waveform data that are input to the microcomputer 10 via the position-detecting panel 27 as instructed by the operator. The liquid crystal display unit 5 further displays the intensity of surface pressure and the contents (size and position) of that flaw that are the results of the flaw detection. The display is instructed by the microcomputer 10, and the contents of display are the data produced by the microcomputer 10. The output data are the results of arithmetic operation when they pertain to the contents of the flaw or the intensity of surface pressure. The data such as waveform data represent values instructed by the position-detecting panel 27.

The keyboard 7 has keys for instructing the contents of measurement for composite measurement, and keys for inputting numerical figures. Keys of the keyboard 7 are turned on or off being manipulated by the operator. The keyed contents of the keyboard 7 are input to the microcomputer 10. The microcomputer 10 receives "turn on" of the manipulated key produced by the keyboard 7, and discriminates and processes the manipulated content. Then, the microcomputer 10 causes the liquid crystal display unit 5 to produce necessary display.

The printer 9 prints the contents instructed by the microcomputer 10. The printer may print the contents displayed on the liquid crystal display unit 5, or may selectively print the contents. The former is useful when the operation procedure is to be followed, and the latter is helpful when necessary results only are to be printed.

The A/D converter 8 receives X-coordinate signal and Y-coordinate signal of a wave form data from the terminals XT, YT selected by the switch 12, and subjects them to the A/D conversion. The results of A/D conversion are received by the microcomputer 10.

Elements that must be manipulated by the operator include repetitive period setter 4, logarithmic converter 23, keyboard 7, and position-detecting panel 27. The repetitive period setter 4 sets the repetitive period of transmission pulses that must be changed depending upon the material to be inspected and the thickness thereof (instruction A). The logarithmic converter 23 is capable of varying the gain, and sets a maximum amplitude of the waveform that is displayed on the display picture plane of the cathode-ray tube 26. The gain is varied by the operator (instruction F). The gain can be arbitrarily varied by the gain setter (not shown) at the time of measurement.

The operator sets a required key "on" on the keyboard 7 (instruction B). The operator depresses a required position on the position-detecting panel 27 (instruction C). It was already mentioned as to how to manipulate the keyboard 7 and the position-detecting panel 27.

The liquid crystal display unit 5 need not be manipulated by the operator. Instead, the operator visually reads the displayed contents (instruction D).

At the time of calibration, a standard test piece is placed instead of the material 30 to be inspected, to take the measurement.

Figure 2:
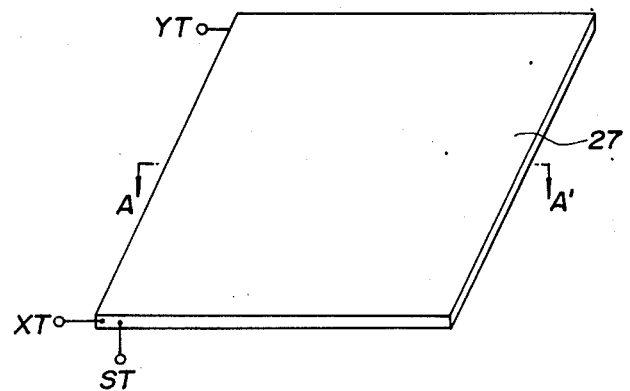
FIG. 2 is a perspective view of a panel for detecting the positions.

FIG. 2 is a perspective view of the position-detecting panel 27 which is made of a transparent material. Even when it is mounted on the display plane of the cathode-ray tube 26, the waveforms on the display surface can be observed through the panel 27. Further, the panel 27 has flexibility and can be fitted to the display plane. The panel 27 has X- and Y-output terminals XT, YT, and a power-source terminal ST.

The position-detecting panel 27 is a transparent touch sensor which, when the observer depresses a given position by a pointer (not shown) or by hand, produces a signal that represents the X-coordinate of the depressed position through the terminal XT, and produces a signal that represents the Y-coordinate thereof through the terminal YT.

Figure 3:
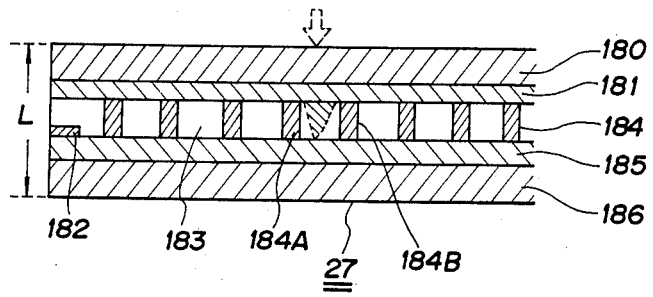
FIG. 3 is a diagram showing the construction of a layer of the panel.

FIG. 3 is a section view of the position-detecting panel 27 along the line A—A' of FIG. 2. The panel 27 has a thickness L of about 0.1 mm in the direction of layer thereof. On the surface of a transparent resin layer 186 made of an acrylic resin or the like, there is formed a resistance layer 185 which has a uniform resistivity in the directions of plane thereof. The resistance layer 185 is transparent. The transparency stands for both when the material of resistor is transparent, and when the resistance layer is as thin as to appear transparent. Either case may be employed depending upon the requirement.

An X-axis electrode is formed on one of the two rectangular sides among the four sides of the resistance layer 185, and a Y-axis electrode is formed on the other side. In FIG. 3, only one electrode is shown as designated at 182.

On the surface of the resistance layer 185 is formed a transparent electrode layer 181 via insulating spacers 184 which are dot-like, which have elasticity in the direction of the length, which contract when depressed from the upper direction, and which are transparent. The spacers 184 are regularly arranged in the vertical and horizontal directions. Thickness and arranged distance of the spacers 184 affect the precision for detecting the positions. Namely, the precision for detecting the positions increases when the spacers 184 are thin and the distance of arrangment is large. Further, thickness of the spacer 184 corresponds to the area of non-sensitive zone. As a matter of course, space 183 is formed among the spacers 184.

A transparent resin layer 180 such as of acrylic resin is formed on the surface of the electrode layer 181.

The position-detecting panel 27 is formed by the thus constituted layers.

If a point on the surface of the position-detecting panel 27 is depressed in the direction of arrow, spacers 184A, 184B of the depressed portion are compressed, and a portion of the electrode layer 181 comes into contact with a portion of the resistance layer 185. Therefore, the electrode 181 and the resistance layer 185 come into point contact with each other to form an electric circuit. The position of point contact can be taken out as a signal of X-coordinate and Y-coordinate via the terminals XT, YT.

Figure 4:
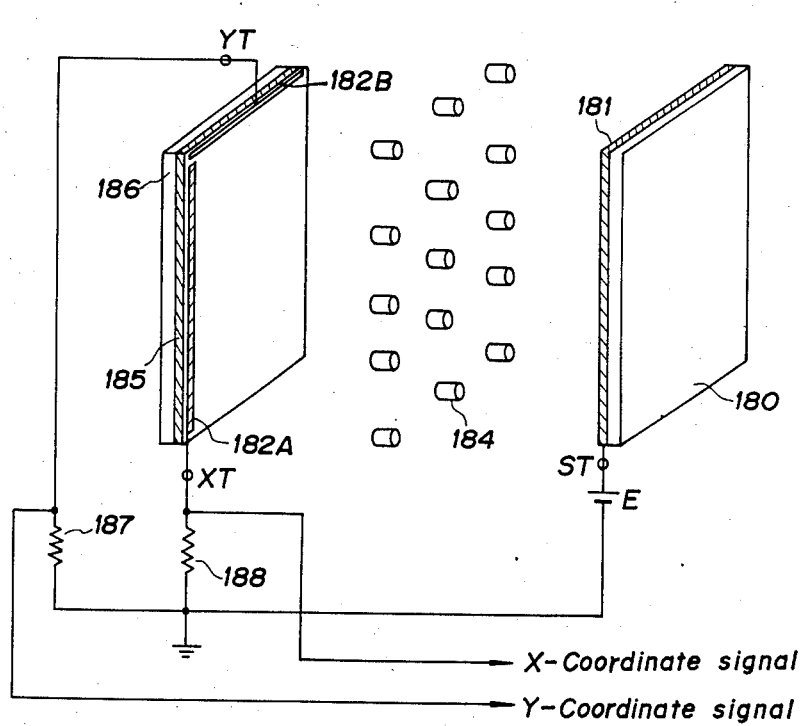
FIG. 4 is a disassembled view of the panel.

FIG. 4 is a diagram which explains the position-detecting panel 27. The electrode 182A for X-axis and the electrode 182B for Y-axis are formed along the two rectangular sides of the resistance layer 185. A transparent electrode layer 181 is provided to oppose thereto via the insulating spacers 184. The transparent electrode layer 181 is provided on the whole surface of the acrylic resin layer 180 on the side of the spacers.

A DC power source E is applied to the electrode layer 181. A resistor 188 is connected between the electrode layer 182A for X-axis and ground, and a resistor 187 is connected between the electrode layer 182B for Y-axis and ground. If a point on the acrylic resin layer 180 is depressed, a point of the electrode layer 181 and a point of the resistance layer 185 establish an electric circuit via a corresponding space 183. The position of the point of this circuit in the Y-direction of coordinate appears on the Y-electrode 182B as a signal corresponding to said position, and the position in the X-direction appears on the X-electrode 182A as a signal corresponding to said position. Therefore, the X-coordinate signal X is detected via an end of the resistor 188, and the Y-coordinate signal is detected via an end of the resistor 187.

Figure 5:
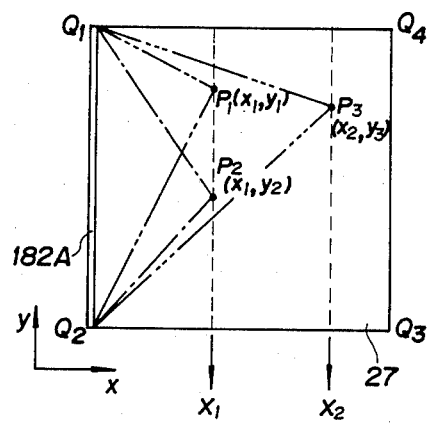
FIGS. 5 and 6 are diagrams illustrating the operation of the FIG. 1 apparatus.
Figure 6:
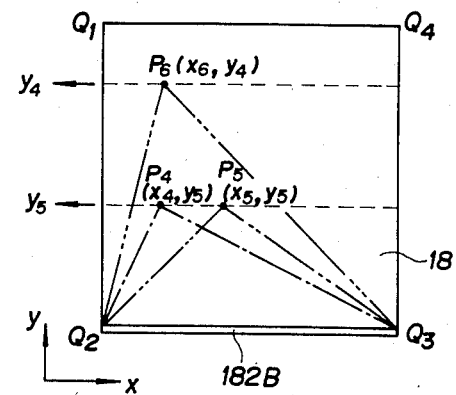

FIG. 5 is a diagram for detecting x-direction coordinate on the position-detecting panel 27, and FIG. 6 is a diagram for detecting y-direction coordinate on the position-detecting panel 27. In FIG. 5, it is presumed that the three points $P_1(x_1, y_2)$, and $P_3(x_2, y_3)$ are depressed separately. The electric currents flow from the power source along the electric circuits formed by depressing the panel 27. The resistance layer 185 of the panel 27 has uniform resistance. When the point $P_1$ is depressed, therefore, an electric circuit proportional to the area of a triangle $Q_1P_1Q_2$ flows into the X-axis electrode 182A, and is taken out. When the point $P_2$ is depressed, an electric current proportional to the area of a triangle $Q_1P_2Q_2$ flows through the electrode 182A. Since $\Delta Q_1P_1Q_2 = \Delta Q_1P_2Q_2$, the same electric current is obtained from the electrode 182A irrespective of the point of depression, provided the point of depression lies along a line $x=x_1$. When the point $P_3$ $(x_2, y_3)$ on a line $x=x_2$ is depressed, a signal proportional to the area of a triangle $Q_1P_3Q_2$ is obtained, the signal corresponding to $x_2$. According to FIG. 5, therefore, a signal that represents the x-coordinate is obtained from the electrode 182A.

The same also holds true in FIG. 6. As for two points $P_4(x_4, y_5)$ and $P_5(x_5, y_5)$ on $y=y_5$, the same electric current corresponding to $y=y_5$ is obtained via the electrode 182B, since $\Delta Q_2P_4Q_3 = \Delta Q_2P_5Q_3$. As for a point $P_6(x_6, y_4)$, an electric current corresponding to $Y=y_4$ is obtained via the electrode 182B.

Figure 7:
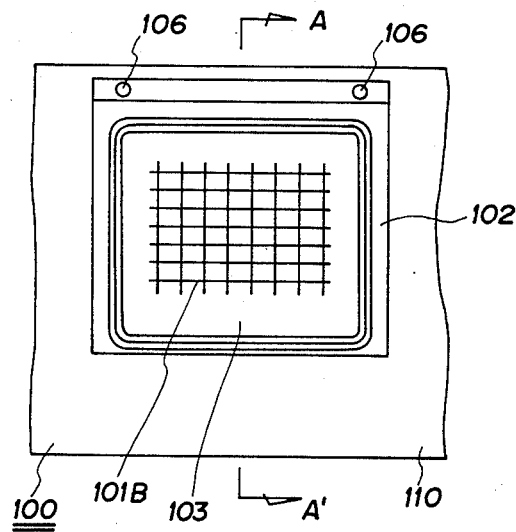
FIG. 7 is a front view of the position-detecting panel mounted on the cathode-ray tube.
Figure 8:
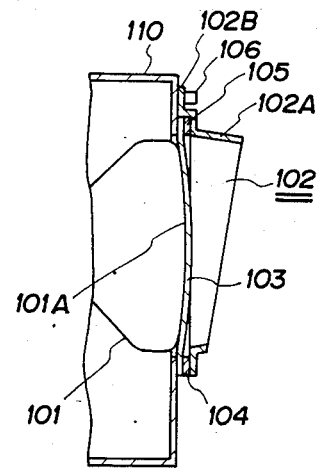
FIG. 8 is a section view along the line A—A' of FIG. 7.

FIGS. 7 and 8 show an embodiment in which the position-detecting panel is mounted on a synchroscope device 100, wherein FIG. 8 is a section view along the line A—A' of FIG. 7.

The synchoscope device 100 has a case 110 with an opening formed in the front surface thereof. The front surface (glass tube) 101A of the cathode-ray tube 101 is inserted in the opening. The front surface 101A is outwardly curved to form a display surface on which observation wave forms will be displayed. The position-detecting panel 103 has an area that is large enough to protrude beyond the front surface 101A. The position-detecting panel 103 is transparent and is flexible, and is hence mounted along the curved portion of the front surface 101A.

A hood 102 is provided to allow observation of the display surface when the measuring apparatus is used outdoors under direct rays of the sun. The hood 102 consists of a case 102A and a seat 102B, the case 102A being protruded in a direction nearly at right angles with the display surface. The upper portion of case 102A is longer than the lower portion thereof. The periphery of the case is so large so to cover the whole area of the display surface.

The seat 102C works to secure the position-detecting panel 103 to the display surface. A packing 105 is inserted in space between the seat 102B and the position-detecting panel 103 thereby to hold the position-detecting panel 103. The seat 102B has holes in the upper portion thereof, and bolts 106 are inserted in the holes to fasten the seat 102B to the case 110. Thus, the position-detecting panel 103 is secured in position, and the hood 102 is secured, too.

FIG. 7 shows the display surface of the cathode-ray tube when it is looked at from the front side. The vertical and horizontal scales 101B on the display surface of the cathode-ray tube can be observed through the position-detecting panel 103. Therefore, the observation waveforms can be observed by the operator, the waveform data can be instructed, and the numerical values can be obtained.

Figure 9:
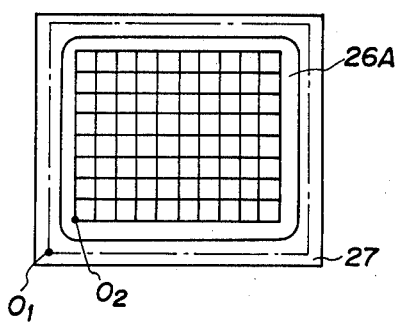
FIG. 9 is a diagram explaining the detection of position.

FIG. 9 is a diagram showing a relationship between the coordinate system of the display picture plane 26A and the coordinate system of the position-detecting panel 27. In FIG. 9, a point $O_2$ represents an origin of a coordinate system on the display plane of the cathode-ray tube, and $O_1$ represents an origin of a coordinate system of the position-detecting panel. The origin $O_1$ of the coordinate system of the position-detecting panel is the one which is determined from the standpoint of measurement, and the origin $O_2$ of the coordinate system of observation waveform is the one determined for the coordinate system for practical measurement. Therefore, it becomes necessary to convert the coordinate system of the position-detecting panel into the coordinate system of display plane. The coordinate conversion is effected by the microcomputer according to software. Here, the equation of coordinate conversion may be an equation of parallel translation.

Figure 10:
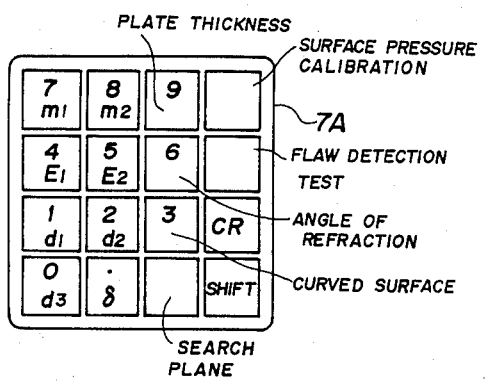
FIG. 10 is a diagram illustrating the arrangement of keys on the keyboard.

FIG. 10 shows an operation panel 7A of the keyboard 7. The panel 7A has a role to input the measuring mode, various constants of objects to be measured, measuring conditions, and the like. The panel 7A will be manipulated by the operator. Peak values of measured waveforms displayed on the cathode-ray tube and beam path are input to the microcomputer 10 via the detecting panel 27 under the condition as instructed by the panel 7A. When the operation are to be carried out, the content that is to be operated next is displayed on the liquid crystal display unit 5, and the operator performs the operation according to the content that is instructed.

The individual keys have the functions as described below.

(1) SHIFT Key:

The keys shown in FIG. 10 all have double functions, except the SHIFT key and the CR key. The SHIFT key is to select either one of the double functions. When the operation of the system is initiated, each of the keys performs the first function (designation on the upper side of the key). When the SHIFT key is depressed once, each of the keys performs the second function (designation on the lower side of the key). When the SHIFT key is depressed once again, the function returns to the first function. Thus, the function is replaced by the other one after every depress of the SHIFT key. The present function of the key being manipulated is displayed on the liquid crystal display unit 5 at all times.

(2) CR Key:

When a variety of constant and data are to be input, the CR key is depressed at the end of a series of data or codes, to finish the data or instruction codes. For instance, when a data, i.e., "plate thickness of 150 mm" is to be input, the keys are depressed in the order of [PLATE THICKNESS], [SHIFT], [1], [5], [0] and [CR]. However, the CR key needs not be depressed in the case of the SHIFT key.

(3) SURFACE PRESSURE Key (first function):

The mode of surface pressure measurement is designated at the time of initiating the operation of the system and at the time of determining the measuring mode for converting the operation mode. The SURFACE PRESSURE key is depressed when the surface pressure is to be measured.

Measurement of surface pressure has been closely described in a patent application entitled "Method of Measuring Contact Stress on a Solid Contact Surface by Ultrasonic Waves" (PCT/JP82/00087) filed by the applicant of the present application.

(4) CALIBRATION Key (second function):

This key is used at the time of initiating the operation of the system and at the time of determining the measuring mode for converting the operation mode. This key designates to calibrate (determine the reference sensitivity) the height of echo of a JIS standard specimen.

(5) FLAW DETECTION Key (first function):

This key is used at the time of initiating the operation of the system and at the time of determining the measuring mode for converting the operation mode. This key designates to effect the flaw detection.

(6) TEST Key (second function):

This key is used at the time of initiating the operation of the system and at the time of determining the measuring mode for converting the operation mode. This key designates to check the operation of the apparatus (particularly, to check the operation of the microprocessor in the microcomputer).

(7) PLATE THICKNESS Key (second function):

This key is used to designate the plate thickness of a material that is to be measured. For instance, when the plate thickness of 15 mm is to be designated, the keys are depressed in the order of [PLATE THICKNESS], [SHIFT], [1], [5], [CR].

(8) ANGLE OF REFRACTION Key (second function):

This key is used to designate the angle of refraction of ultrasonic waves determined by a proble. The angle of refraction is designated by manipulating the keys in the same manner as mentioned in (7) above.

(9) CURVED SURFACE Key (second function):

In measuring the surface pressure, this key designates that the surface being measured is a curved surface. The operator depresses the keys in the order of [CURVED SURFACE], [CR].

(10) PLANE Key (second function):

In measuring the surface pressure, this key designates that the surface being measured is a plane. The operator depresses the keys in the order of [PLANE], [CR].

(11) SEARCH Key (first function):

This key is used to search the desired S echo and R echo in the surface-wave method of mode conversion. For instance, the keys are depressed in the order of [SEARCH], [CR].

(12) 0, 1, - - - , 9 Keys (first functions):

These keys are used to set a variety of data, constants, codes, and the like.

(13) [.] Key (first function):

This key is used to designate a decimal point.

(14) $m_1$, $m_2$, $E_1$, $E_2$, $d_1$, $d_2$, $d_3$, $\delta$ Keys (second functions):

These keys are used to set the constants for the equations for judging whether the pressure of the contacted surface is acceptable or not. The contents are as follows:

$m_1$, $m_2$—Poisson's ratios,
$E_1$, $E_2$—Young's moduli,
$d_1$—inner diameter of bushing,
$d_2$—outer diameter of bushing,
$d_3$—outer diameter of boss,
$\delta$—tightening margin.

The ultrasonic flaw detection of the thus constructed A-scope system is carried out as described below.

Figure 11A:
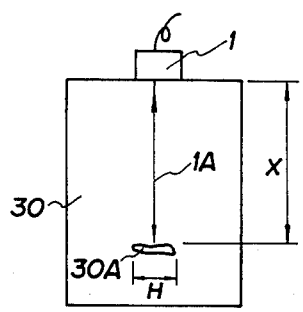
FIGS. 11(A), 11(B) and 11(C) are diagrams illustrating the A-scope.
Figure 11B:
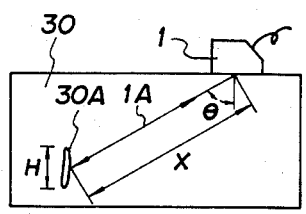

According to the ultrasonic flaw detecting method based upon the A-scope system, ultrasonic waves 1A emitted from the probe 1 are allowed to be incident upon a material 30 to be inspected such as steel or copper alloy, as shown in FIGS. 11(A) and 11(B), and the reflected waves (hereinafter referred to as echo) from a defect 30A in the material 30 being inspected are received by the probe 1. The echo is then amplified, detected, and is displayed on the picture plane of the cathode-ray tube. The amplitude of the echo and the time for obtaining the echo (time required for transmitting and receiving the ultrasonic waves) are measured to detect the size and position of defect.

This method can be divided into a vertical flaw detecting method according to which the ultrasonic waves are allowed to be incident perpendicularly upon the surface of the material 30 to be inspected as shown in FIG. 11(A), and a tilted-angle flaw detecting method according to which the ultrasonic waves are allowed to be incident obliquely at an angle $\theta$ of refraction as shown in FIG. 11(B).

The probe usually employs a frequency ranging from 2 to 5 MHz, and the transducer employed therein has a size ranging from 5 to 20 mm in diameter. In the angle beam flaw detection method, the angle of refraction in many cases ranges from 40° to 70°. The vertical flaw detecting method employs longitudinal waves, and the angle beam flaw detecting method employs transversal waves.

Figure 11C:
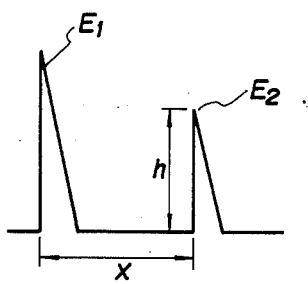

The abscissa (X-axis) represents the time and the ordinate (Y-axis) represents the amplitude on the cathode-ray tube. When a defect exists, an echo $E_2$ of an amplitude h is obtained at a position x on the X-axis as shown in FIG. 11(C). A wave $E_1$ represents a pulse signal that is transmitted. The value x on the cathode-ray tube corresponds to a distance x between the probe and the defect shown in FIGS. 11(A), 11(B). Therefore, the position of defect can be found from the value x on the cathode-ray tube. Generally, the amplitude h of echo is proportional to the size H of defect and, hence, the size of defect can be measured from the amplitude of echo.

To designate the position of the A-scope system using the position-detecting panel, the position x where the reflected wave (echo) $E_2$ occurs should be depressed, and the position (peak point) of amplitude h of the echo $E_2$ should be depressed to input the data to the microcomputer 10. The position x where the echo occurs and the peak point (amplitude h) vary depending upon the material to be inspected and the contents of inspection. These positions can be easily designated owing to the provision of the position-detecting panel 27, and can be input to the computer.

When the position and size of defect are to be found by the ultrasonic flaw detection based upon the A-scope system, it is necessary to know the distance of echo (referred to as beam path) on the X-axis and the amplitude (referred to as height of echo) in the direction of Y-axis on the cathode-ray tube.

The beam path of echo and the height of echo obtained by the ultrasonic flaw detection do not represent absolute values, but are relative values. Therefore, the X-axis and Y-axis on the cathode-ray tube must be calibrated prior to effecting the flaw detection by using a standard test block or control test piece.

Calibration is effected using, for example, a JIS test block 30B which is shown in FIGS. 12(A), 12(B) and 12(C). FIG. 12 shows a standard test block of G-type sensitivity for ultrasonic flaw detection specified under JIS Z 2345. This test block is used for the vertical flaw detection. Using this test piece, the calibration is effected as described below.

Namely, the probe is brought into contact with the end of the test block, to produce echo $E_2$ reflected from the hole of $\phi 2$ with a flat bottom and echo $E_3$ reflected from the bottom surface as shown in FIG. 12(C). FIG. 12(C) shows the wave forms displayed on the display plane 26A.

Next, the X-axis adjusting knob of the flaw detector is manipulated, such that the echo from $\phi 2$ comes to a position of 80 mm on the X-axis and the echo from the bottom surface comes to a position of 100 mm. Thus, the calibration of X-axis is completed.

Then, the Y-axis adjusting knob is so adjusted that the height of echo from 100 2 is set to 50% of the full scale (100%). The value of knob serves as a reference height of echo. Thus, the calibration is completed in the direction of Y-axis.

In the case of the angle beam flow detection, use is made of an STB-A1 test block in compliance with JIS Z 2347 and an STB-A2 test block in compliance with JIS Z 2348, to calibrate the beam path and the height of echo, respectively. The calibration is effected quite in the same manner as that of the aforementioned vertical flaw detection.

Operations are explained below using the keyboard 7.

(A) Operation for setting the initial condition.
(B) Calibration operation.
(C) Measurement of surface pressure.
(D) Flaw detection.

These operations will be described below in detail.

(A) Setting of initial condition using the keyboard 7.

After some time has passed from the closure of the power source, the liquid crystal display unit 5 displays "SYSTEM READY E=1 OPERATION START", letting the operator know that the measuring instrument is ready for operation and is waiting for an instruction by the operator. Here, F=1 represents that the key is selecting the first function. The second function will be represented by F=2. Responsive to this display, the operator performs any one of the following operations.

(A-1) When the surface pressure is to be measured.

The keys are depressed in the order of "SURFACE PRESSURE", "CR".

(A-2) When the flow detection is to be effected.

The keys are depressed in the order of "FLAW DETECTION", "CR".

(A-3) When the calibration is to be effected.

Depress the "SHIFT" key. After having confirmed that F=2 is displayed on the liquid crystal display unit 5, depress the keys in the order of "CALIBRATION", "CR".

(A-4) When the functions are to be tested.

Depress the "SHIFT" key. After having confirmed that F=2 is displayed on the liquid crystal display unit 5, depress the keys in the order of "TEST", "CR".

By effecting any one of the above operations, the measurement is started or the checking of operation is initiated. In setting the initial condition, it is not allowed to designate items other than the above-mentioned items A-1 to A-4.

(B) Then, the calibration is effected using the keyboard 7.

When various measurements are to be taken using the apparatus of the present invention, a reference sensitivity must be found in advance to define the echo level of the reflected waves. Therefore, this operation is carried out prior to taking measurements.

(B-1) When the calibration mode is selected according to the procedure of setting the initial conditions, the display unit displays "INPUT ECHO HEIGHT TO CALIBRATE REFERENCE SENSITIVITY". Ultrasonic waves are input to the test piece which has been prepared, the gain is adjusted by a gain setter 23, and the height of echo (peak value) of the reflected wave is input using the position-detecting panel 27. The height of echo can be input by simply depressing a peak point of echo wave displayed on the display plane 26A.

(B-2) As the height of echo is input, the display unit displays "INPUT HS=** ECHO LEVEL".

Here, HS simply denotes Y-coordinate of a point designated on the touch panel. Therefore, the operator must designate the echo level in dB.

The echo level is input according to the following procedure.

Example: "3", "5", "CR"—when the reference sensitivity is 35 dB.

(B-3) Owing to the operations (B-1), (B-2) mentioned above, the points (distances in the direction of Y-axis) on the scope are defined based upon the reference sensitivity. Further, once the calibration is effected, the calibrated value is stored to be commonly used for all of the modes unless the memory is broken by the drop of power-source voltage.

When the operation (B-2) is finished, the display unit 5 displays "INPUT HS-35 DB BEAM PATH" (but when the reference sensitivity is 35 dB).

(B-4) Beam path for the standard test piece is input using the panel 27. This is done by designating the rising point of the incident wave and the reflected wave. Designation is effected in the order of rising point of the incident wave and rising point of the reflected wave.

As the two points are input, the display unit 5 displays "INPUT X=** BEAM DATA".

Here, symbol X simply stands for a distance of a point on the X-coordinate designated on the touch panel. Therefore, the operator must designate the beam path in millimeters.

The data of beam path is input according to the following procedure.

Example: "7", "5", "CR"—when the beam path for the test piece is 75 mm.

(B-5) Owing to the operation of (B-4), points (distances in the direction of X-axis) on the scope are defined based upon the reference beam path. Once the calibration is effected, the above-defined beam path is maintained valid until the calibration is effected again, in the same manner as mentioned in (B-3).

After the operation (B-5) is finished, the display unit displays "HS=35 DB X=75 MM SYSTEM STAND-BY", to let the operator know that the calibration is finished and that measurement is ready to be taken.

(B-6) After the operations (B-1) to (B-5) have been finished, the operator should select any one of "SURFACE PRESSURE", "FLAW DETECTION", "TEST" or "CALIBRATION".

(C) Measurement of surface pressure is described below.

(C-1) At the time of setting the initial condition, if the mode of surface pressure measurement is selected by the operation (1), the display unit 5 displays "SURFACE PRESSURE MODE STAND-BY F=*(1 or 2) SHAPE? D2?".

The operator designates whether the surface to be measured has the shape of a plane or a curved surface. The operator, further, designates the outer diameter d2 of the bushing according to the following procedure.

Example: "PLANE", "CR", "d2", "3", "0", "CR"—when the contacted surface is a plane with D2=30 mm (function of the key has been displayed on the liquid crystal display unit 5, and use the "SHIFT" key after having confirmed it).

(C-2) Accompanying the operation (C-1), the display unit displays "PLANE D2=30 1:STEEL-STEEL 2:STEEL-GUN METAL". When the contacted surfaces are steel to steel, the operator manipulates the keys in the order of "1", "CR". When the contacted surfaces are steel to gun metal, the operator manipulates the keys in the order of "2", "CR".

(C-3) Accompanying the operation (C-2), the display unit displays "PLANE D2=30 STEEL-GUN METAL H1?".

The operator inputs the peak point of echo using the touch panel 27.

(C-4) Responsive to the operation (C-3), the display unit displays "PLANE D2=30 STEEL-GUN METAL H1=**dB H2?". The operator inputs the peak point of the transmitted wave using the touch panel 27.

(C-5) Owing to the operation (C-4), the arithmetic operation is initiated. When the arithmetic operation is finished, the display unit displays "PRESS*.**KG/MM2 MEAS NO.?". The operator inputs the test number.

(C-6) Responsive to the operation (C-5), the display unit displays "PRESS*.KG/MM2 MEAS. NO.CONST:1 POSITION:2". "2", "CR" are input when the tolerance of surface pressure is to be found depending upon the position number that has been designated beforehand, and "1", "CR" are input when the tolerance of surface pressure is to be found by calculation. The operator selects the code numbers that represent predetermined positions or selects constants "m1", "m2", "d1", "d2", "d3", "E1", "E2", "δ" of the equation for judging whether the pressure of contacted surface is acceptable or not, and inputs them.

Example: "1", "2", "CR"—when code numbers depending upon the positions are to be input.

"d1", "3", "5", "CR"—when the constants are to be specified.

(C-7) Whether the pressure of the contacted surface is acceptable or not is judged by the operation (C-6), and the result is displayed as NO-GO.

Example: "PRESS*.KG/MM2 MEAS. NO. GO".

(C-8) Thus, measurement of the pressure of the contacted surface is completed.

(D) Described below is the flaw detection.

(D-1) When the flaw detection mode is selected by the operation of setting the initial condition (A-2), the display unit displays "FLAW DETECTION MODE STAND-BY F=*(1 or 2) T? θ? MODE?". The operator designates T: plate thickness, θ: angle of refraction, and measuring mode. The plate thickness is designated in millimeters, and the angle of refraction is designated in degrees.

The measuring mode is designated by code as follows, and is concretely described with reference to i to iii.

i. Method of maximum height of echo: 01,
ii. Method of correcting probe distance: 02,
iii. Surface-wave method of mode conversion: 03,
iv. 6-dB drop method: 04,
v. Method of scattered longitudinal waves: 05,
vi. Method of peak echo at the end portion: 06.

Example: When the plate thickness is 15 mm, angle of refraction is 30 degrees, measuring mode is 6-dB drop method, and F=1.

Depress the keys in the order of "SHIFT", "PLATE THICKNESS", "SHIFT", "1", "5", "CR", "SHIFT", "ANGLE OF REFRACTION", "SHIFT", "3", "0", "CR", "0", "4", "CR".

(D-2) Measurement by the method of a maximum height of echo.

When the maximum height of echo method (code 01) is selected by the operation (D-1), the display unit displays "M" ECHO HEIGHT, F=*(1 or 2) T= θ=H?". The operator designates the height of echo using the touch panel 27.

When the height of the echo is designated, the apparatus performs measurement and arithmetic operations, and the display unit displays "M: ECHO HEIGHT F=* H=**MM".

Thus, the measurement is finished by the method of the maximum height of the echo.

(D-3) Mesurement by the method of correcting the probe distance and by the surface-wave method of mode conversion.

When the method of correcting the probe distance (code 02) or the surface-wave method of mode conversion (code 03) is selected by the operation (D-1), the display unit displays "M: CORRECT DISTANCE (SURFACE WAVE) F=*(1 or 2) T= θ=AUTO?". This mode has a function to automatically determine whether the arithmetic operation be carried out by the method of correcting the probe distance or by the surface-wave method of mode conversion depending upon the designated plate thickness. It is of course allowable to determine the method of measurement and arithmetic operation irrespective of the plate thickness, depending upon the judgement by the operator.

In the case of the automatic measurement (method of arithmetic operation is automatically determined by the plate thickness), the operator depresses the key "1". Otherwise, the operator depresses the key "2".

Example: In the case of automatic measurement (select F=1). "1", "CR".

(D-4) When the automatic mode is selected by the operation (D-3), the following display is produced depending upon the designated plate thickness.

(D-4-1) When the plate thickness of smaller than 6 mm is designated.

(a) The display unit displays "M: CORRECT DISTANCE F=*(1 or 2) H?".

The operator inputs the height of echo using the touch panel.

As the height of echo is designated, the apparatus performs the measurement and arithmetic operation, and the display unit displays "H=**MM MODE: CORRECT DISTANCE", and the measurement is completed.

(D-4-2) When the plate thickness is greater than 6 mm but is smaller than 28 mm.

(a) The display unit displays "M: CORRECT DISTANCE F=*(1 or 2) AUTO: 0 SURFACE: 1 INTERNAL: 02".

According to this mode, the depth of defect is automatically calculated, and the defect is displayed whether it exists on the surface or in the internal portion. When it is judged by the operator that the defect exists on the surface or in the internal portion, it can be designated by a key.

When the depth of defect is to be automatically calculated depending upon the above display, the keys "0", "CR" are depressed. When it is judged that the defect exists on the surface, the keys "1", "CR" are depressed. When it is judged that the defect exists in the internal portion, the keys "2", "CR" are depressed.

(b) When "0", "CR" are selected (automatic mode).

(b-1) The display unit displays "M: CORRECT DISTANCE F=*(1 or 2) X?". The operator inputs the difference of beam distance of echo by using the touch panel. The input designates the rising point of echo.

(b-2) The depth of defect is calculated by the operation (b-B 1), and the display unit displays "M: CORRECT DISTANCE F=*(1 or 2) D=**MM SURFACE (INTERNAL)H?". The operator inputs the height of echo using the touch panel.

(b-3) Due to the operation (b-2), the display unit displays "M: CORRECT DISTANCE F=*(1 or 2) D=MM SURFACE (INTERNAL) H=MM", and the measurement is completed.

(c) When "1", "CR" are designated by the operation (D-4-2) (a) (when the surface defect is designated).

(c-1) The display unit displays "M: CORRECT DISTANCE F=*(1 or 2) SURFACE H?". The operator inputs the height of echo using the touch panel.

(c-2) Due to the operation (c-1), the display unit displays "M: CORRECT DISTANCE F=*(1 or 2) SURFACE H=**MM", and the measurement is completed.

(d) When "2", "CR" are designated by the operation (D-4-2) (when the internal defect is designated).

(d-1) The display unit displays "M: CORRECT DISTANCE F=*(1 or 2) INTERNAL H?". The operator inputs the height of echo using the touch panel.

(d-2) Due to the operation (d-1), the display unit displays "M: CORRECT DISTANCE F=*(1 or 2) INTERNAL H=**MM", and the measurement is completed.

(D-4-3) When the plate thickness is greater than 28 mm.

(a) The display unit displays "M: SURFAE WAVE F=*(1 or 2) AUTO: 0 SURFACE: 1 INTERNAL: 2". This mode automatically calculates the depth of defect and displays whether the defect exists on the surface or in the internal portion. When the operator can judge that the defect exists on the surface or in the internal portion, it can be designated by the key.

When the depth of defect is to be automatically calculated depending upon the above display, the keys "0", "CR" are depressed. When it is judged that the defect exists on the surface, the keys "1", "CR" are depressed. When it is judged that the defect exists in the internal portion, the keys "2", "CR" are depressed.

(b) When "0", "CR" are selected (automatic mode).

(b-1) The display unit displays "M: SURFACE WAVE F=*(1 or 2) X?". The operator inputs the beam distance of S echo using the touch panel. The input designates a rising point of S echo.

(b-2) The depth of defect is calculated by the operation (b-1). When the defect exists on the surface, the display unit displays "M: SURFACE WAVE F=*(1 or 2) D=**MM SURFACE H?". The operator inputs the height of S echo using the touch panel.

Measurement and arithmetic operation are then carried out, and the display unit displays "M: SURFACE WAVE F=*(1 or 2) D=MM SURFACE H=MM", and the measurement is completed.

(b-3) The depth of defect is calculated by the operation (b-1). In the case of the internal defect, the display unit displays "M: SURFACE WAVE F=*(1 or 2) D=**MM INTERNAL SURFACE: 1 SPHERE: 2". When the defect exists in the form of a plane, the operator depresses the keys B "1", "CR". When the defect exists in the form of a sphere, the operator depresses the keys "2", "CR".

(b-4) Due to the operation (b-3), the display unit displays "M: SURFACE WAVE F=*(1 or 2) D=** INTERNAL SURFACE (SPHERE) DX?". The operator inputs beam distances of S echo and R echo using the touch panel. The order of inputs consists of a rising point of S echo and a rising point of R echo.

(b-5) Arithmetic operation is initiated by the operation (b-4), and the display unit displays "M: SURFACE WAVE F=*(1 or 2) D=MM INTERNAL SURFACE (SPHERE) H=MM", and the measurement is completed.

(c) When "1", "CR" are designated by the operation (D-4-3) (a) (when the defect on the surface is designated).

(c-1) The display unit displays "M: SURFACE WAVE F=*(1 or 2) SURFACE H?". The operator inputs the height of S echo using the touch panel 27.

(c-2) Arithmetic operation is performed by the operation (c-1), the display unit displays "M: SURFACE WAVE F=*(1 or 2) SURFACE H=**MM", and the measurement is completed.

(d) When "2", "CR" are designated by the operation (D-4-3) (a) (when the internal defect is designated).

(d-1) The display unit displays "M" SURFACE WAVE F=*(1 or 2) INTERNAL SURFACE: 1 SPHERE: 2". The operator depresses the keys "1", "CR" when the defect assumes the shape of a plane, and depresses the keys "2", "CR" when the defect assumes the shape of a sphere.

(d-2) Due to the operation (d-1), the display unit displays "M: SURFACE WAVE F=*(1 or 2) INTERNAL SURFACE (SPHERE) DX?". The operator inputs beam distances of S echo and R echo using the panel 27. The order of inputs consists of a rising point of S echo and a rising point of R echo.

(d-3) Arithmetic operation is initiated by the operation (d-2), the display unit displays "M: SURFACE WAVE F=*(1 or 2) INTERNAL SURFACE (SPHERE) H=**MM", and the measurement is completed.

The S echo and R echo are used for the surface-wave method of mode conversion mentioned in (D-3) above. In general, however, since complex waveforms are displayed on the cathode-ray tube, the desired echo can be found requiring tremendous effort. However, the mode of the invention has a function to find the S echo and R echo, so that anybody can take the measurement easily. The operator finds the desired S echo and R echo according to the following procedure.

(a) The surface-wave method of mode conversion or the method of correcting the probe distance is selected as a measuring mode, and then the keys are depressed in the order of [SEARCH] and [CR].

(b) Due to the operation (a), the display unit displays "M: SURFACE WAVE (CORRECT DISTANCE) F=*(1 or 2) S1? R1?". The operator designates rising portions of wave forms that are considered to be those of the S echo and R echo using the panel 27. The order of designation consists of a rising point of S echo and a rising point of the R echo.

(c) Due to the operation (b), the display unit displays "M: SURFACE WAVE (CORRECT DISTANCE) F=*(1 or 2) SEARCH S2? R2?". The operator manipulates the probe to move the S echo and R echo, and designates again the rising portions of the S echo and R echo using the touch panel 27. The order of designation consists of a rising point of the S echo and a rising point of the R echo.

(d) Arithmetic operation is initiated by the operation (c). When the difference is smaller than 10% between the beam path difference designated in (b) and the beam path difference designated in (c), the symbol OK is displayed. In other cases, the symbol NO is displayed.

The display unit displays "M: SURFACE WAVE (CORRECT DISTANCE) F=*(1 or 2) SEARCH OK(NO) E:1R:2T:3". When the S echo and R echo are found through the operation effected twice, the search is completed. The apparatus of the invention is provided with a function to effect the checking three times, and a function to effect the checking from the first time.

The operator designates the measurement that is to be effected next in accordance with the procedure mentioned below.

Here, however, the function to effect the checking three times is effective only when the results of checking that had been effected twice are acceptable (OK).

(d-1) To end the search—depress the keys in the order of "1", "CR".

The measuring apparatus returns to the condition of before the search is initiated.

(d-2) To effect the checking again from the first time—depress the keys in the order of "2", "CR".

(d-3) To effect the checking of the third time—depress the keys in the order of "3", "CR".

(e) When "2", "CR" are selected by the operation (d), the display unit displays "M: SURFACE WAVE (CORRECT DISTANCE) F=*(1 or 2) SEARCH S1? R1?". The operator repeats the operations (b), (c) and (d), so that search is carried out.

(f) When "3", "CR" are selected by the operation (d), the display unit displays "M: SURFACE WAVE (CORRECT DISTANCE) F=*(1 or 2) SEARCH S3? R3?". The operator operates the probe to move the position of the echo, and then designates beam paths of waveforms that are considered to be those of the S echo and R echo.

The order of designation consists of a rising portion of the S echo and a rising portion of the R echo.

(g) Arithmetic operation is carried out by the operation (f). When the difference is smaller than 10% between an average value of data that has been measured twice and a value measured in the third time, OK is displayed. In other cases, NO is displayed, in the following manner.

"M: SURFACE WAVE (CORRECT DISTANCE) F=*(1 or 2) SEARCH OK(NO) E: 1 R: 2"

(h) Checking function is completed three times by the operation (g). To end the search, depress the keys "1", "CR". To effect the checking again from the first time, depress the keys "2", "CR".

(h-1) When the keys "1", "CR" are depressed, the condition (d-1) is established.

(h-2) When the keys "2", "CR" are depressed, the operation (e) is effected.

(D-5) Measurement by the 6-dB drop method.

When the 6-dB drop method (code 04) is selected by the operation (D-1), the display unit displays "M: 6 DB F=*(1 or 2) T= $\theta$=X?". Different measuring method will be employed depending upon when the angle ($\theta$) of refraction is 0° (vertical flaw detection) and when the angle ($\theta$) of refraction is not 0° (angle beam flaw detection).

(D-5-1) In the case of vertical flaw detection.

(a) Operate the probe to find the highest point of echo. In this case, input the beam path X. The order of inputs consists of a rising point of incident wave and a rising point of reflected wave.

(b) Due to the operation (a), the display unit displays "M: 6 DB F=*(1 or 2) T= $\theta$= D=**MM", and the arithmetic operation is completed. The operator, however, operates the probe to find a point that drops by 6 dB from the maximum height of the echo (a point on the right or left side, and a point on the front or back side). The distance between these two points represents the height H of defect.

(c) Thus, the measurement is completed.

(D-5-2) In the case of the angle beam flaw detection.

(a) The probe is operated to find a point at which the height of the echo becomes maximum, and the beam path in this case is input using the panel 27. The order of inputs consists of a rising point of incident wave and a rising point of reflected wave.

(b) Due to the operation (a), the display unit displays "M: 6 DB F=*(1 or 2) T= $\theta$= D=**MMX1?". The operator operates the probe to find a point where the height of echo drops by 6 dB from a maximum height of the echo, and inputs the beam path by using the panel 27. The order of inputs consists of a rising point of incident wave and a rising point of reflected wave.

(c) Due to the operation (b), the display unit displays "M: 6 DB F=*(1 or 2) T= $\theta$= D=**X2?". The operator operates the probe to find another point at which the height of the echo drops by 6 dB from the maximum height of the echo on a side opposite to the side of the point found in (b) above, and inputs the beam path using the panel. The order of inputs consists of a rising point of incident wave and a rising point of reflected wave.

(d) Due to the operation of (c), the display unit displays "M: 6 DB F=*(1 or 2) T= $\theta$= D=MM H=MM", and the measurement is completed.

In carrying out the 6 dB-drop method, it is recommended to set an alarm bell at a point which is 6 dB lower than the maximum height of the echo by manipulating a knob at the upper portion of the measuring apparatus, so that a desired position of probe can be known without the need of observing the height of the echo.

(D-6) Measurement by the method of scattered longitudinal waves.

When the method of scattered longitudinal waves (code 05) is selected by the operation (D-1), the display unit displays "M: LONGITUDINAL WAVE F=*(1 or 2) T=** $\theta$=OX?DX?". The operator inputs the beam distances of the U echo and L echo using the touch panel. The order of inputs consists of a rising point of incident wave, a rising point of the U echo and a rising point of the L echo.

Due to the above operation, arithmetic operation is initiated, and the display unit displays "M: LONGITUDINAL WAVE F=*(1 or 2) T= $\theta$=O H=MM D=**MM", to complete the measurement.

(D-7) Measurement by the method of peak echo at end portions.

(a) When the method of peak echo at end portions (code 06) is selected by the operation (D-1), the display unit displays "M: PEAK F=*(1 or 2) T= $\theta$=X?". The operator inputs the beam path X using the touch panel. The order of inputs consists of a rising point of incident wave and a rising point of reflected wave.

(b) Responsive to the operation (a), the display unit displays: "M: PEAK F=*(1 or 2) T= $\theta$= D=**MM INTERNAL: 1 OPENING: 2". The operator judges whether the defect is in the internal portion or is an opening defect on the surface. In the case of an opening defect on the surface, the operator depresses the keys "2", "CR". In the case of the internal defect, the operator depresses the keys "1", "CR".

(c) When "1", "CR" are input by the operation (b) (when it is judged that the defect exists in an internal portion), the display unit displays "M: PEAK F=*(1 or 2) T= $\theta$=X1?".

(c-1) The operator operates the probe, and inputs the beam path X1 of the peak echo from the end of defect using the touch panel. The order of inputs consists of a rising point of the incident wave and a rising point of the peak echo.

(c-2) Due to the operation (c-1), the display unit displays "M: PEAK F=*(1 or 2) T= $\theta$=X2?". The operator operates the probe again to input the beam path X2 peak echo from another end of defect using the touch panel. The order of inputs consists of a rising point of incident wave and a rising point of the peak echo.

(c-3) Due to the operation (c-2), the height H of the echo is calculated, the depth D of the defect is calculated again, and the measurement is completed.

(d) When "2", "CR" are input by the operation (b) (when it is judged that the defect is an opening defect on the surface), the display unit displays "M: PEAK F=*(1 or 2) T= $\theta$= UPPER: 1 LOWER: 2". The operator depresses the keys "1", "CR" when the opening portion of defect exists on the upper surface of the material being measured, and depresses the keys "2", "CR" when the opening portion of the defect exists on the lower surface of the material being measured.

(e) Due to the operation (d), the display unit displays "M: PEAK F=*(1 or 2) T= $\theta$= X?". The operator inputs the beam distance X from the end of defect to the reflected wave (peak echo) using the panel 18.

The order of inputs consists of a rising point of incident wave and a rising point of reflected wave (peak echo).

(f) Due to the operation (e), the display unit displays "M: PEAK F=*(1 or 2) T= $\theta$= D=MM H=MM", and the measurement is completed.

Items and contents of measurement are described below briefly.

(A) Function to measure the pressure of contact surface.

When ultrasonic waves are applied onto a surface S to which a metal is contacted maintaining a given pressure, there exists a correlation between the pressure of contacting surface and the ratio of sound pressures of waves reflected from the contacting surface S and from the bottom surface B. Utilizing this principle, the pressure P of contacting surface is found. A bearing will be described below being constituted by a boss 32 made of a steel and a bush 31 made of a sintered metal as shown in FIG. 13. When the intensity of wave reflected from the bottom surface of boss is denoted by $h_1$, and the intensity of wave reflected from the bottom surface of bush by $h_2$, the pressure P of the contacting surface is given by the following equation (1).

$$P \propto \frac{h_1}{h_2} \quad (1)$$

There are numerous equations depending upon the material of a portion that is to be measured and the shape thereof. Different equations will be employed depending upon when the surface to be measured is a curved surface, and when the surface to be measured is a plane. Further, the equation will have to be modified when the contacting surfaces are steel to steel, or steel to gun metal. The equations to cope with the material of a portion to be measured and the shape thereof, are selected by the operator by depressing the keys on the keyboard.

(B) Function to judge whether the pressure of contacting surfaces is acceptable or not.

A setpoint value of tolerance of the pressure of contacting surfaces is found beforehand, and is compared with a measured value found in (A) above to judge whether it is acceptable or not. A setpoint value can be given by the equation (2).

$$P_A = \frac{\delta}{d_2 \left\{ \frac{d_1^2 + d_2^2}{E_1(d_2^2 - d_1^2)} + \frac{d_2^2 + d_3^2}{E_2(d_3^2 - d_2^2)} + \frac{1}{E_2 \cdot m_2} - \frac{1}{E_1 \cdot m_1} \right\}} \quad (2)$$

$d_1$: inner diameter of bushing  
$d_2$: outer diameter of bushing  
$d_3$: outer diameter of boss  
$\delta$: tightening margin  
$E_1$, $E_2$: Young's moduli  
$m_1$, $m_2$: Poisson's numbers The above parameters are input by the operator by manipulating the keys. As for representative portions to be measured, such as surface tightened by bolts, gear portion, bearing of arm, and the like, it is allowable to designate the portions to be measured n order to determine the tolerance of surface pressure.

(C) Function of flaw detection.

Like general flaw detectors, the shape of defect, size and depth thereof are measured by utilizing echoes from the defective portions displayed on the cathode-ray tube.

(C-1) Measuring function by the method of a maximum echo height.

This method is employed when the height of defect is to be found for the pipes of smaller than 6 mm.

Incident waves of a tilted angle are utilized for this method.

In effecting the angle beam flaw detection using a probe having broad-band frequency characteristics for the plates having a thickness of smaller than 6 mm relying upon the method of a maximum echo height, there exists a proportional relation between a maximum echo height and the size of defect. Therefore, the size of defect is found by utilizing this relation (refer to HITACHI HYORON Vol. 64, No. 9, p. 69, 1982).

According to this method, the measuring procedure is as described below.

Figure 15A:
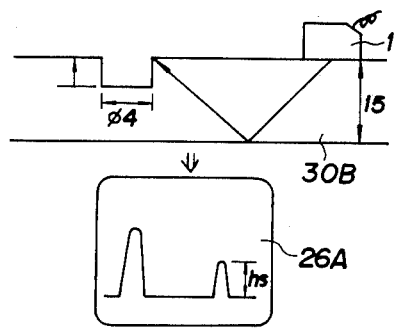
FIGS. 15(A), 15(B), FIGS. 16(A), 16(B), FIGS. 17(A), 17(B), FIG. 18, FIGS. 19(A), 19(B), FIGS. 20(A), 20(B), and FIGS. 21(A), 21(B) are diagrams illustrating the operations of flaw detection.

(i) A reference sensitivity is found using a reference number 30B as shown in FIG. 15(A). The results of display are shown in the lower portions of the drawings. First, a reference sensitivity $h_s$ is found using JIS-STB-A2-$\phi$4 and is stored.

Figure 15B:
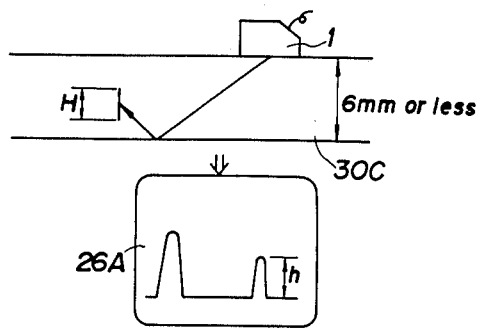

(ii) The height h of the echo of the material 30C being measured is found, as shown in FIG. 15(B), and the height H of the defect is found according to the equation (3).

$$H = 10^{\frac{(h-h_s)-3}{20}} \quad (3)$$

(C-2) Measuring function by the method of correcting probe distance.

In effecting the angle beam flaw detection for the plates having a thickness of 6 mm to 28 mm relying upon the method of correcting probe distance, there exists a proportional relationship among a maximum height of the echo, size of the defect and beam distance (or probe distance). Therefore, the size of defect is found utilizing this relationship (refer to NON-DESTRUCTIVE INSPECTION Vol. 26, No. 5, O. 336, 1977).

This method utilizes angle beam wave technique, and finds the height H of the defect from the maximum height h of the echo and the beam distance X.

Figure 16A:
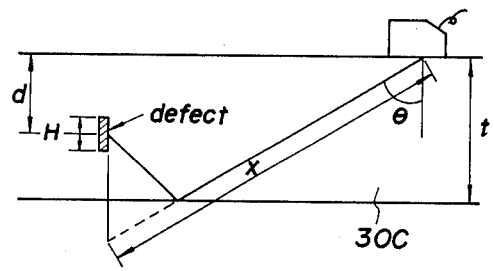
Figure 16B:
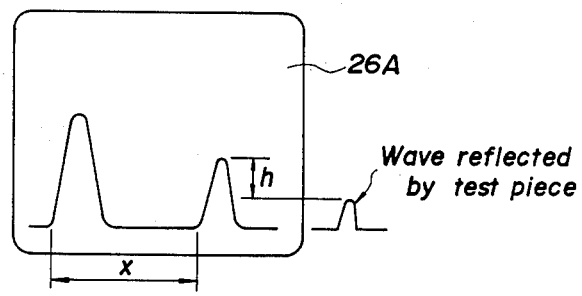

FIGS. 16(A), 16(B) illustrate a fundamental principle of the method of correcting probe distance. In this measurement, the plate thickness, maximum height of the echo, and the like, are designated by the operator. Further, a reference height of the echo must be found using a standard test block in compliance with JIS, and must be stored beforehand.

(i) When the plate to be inspected has a thickness of smaller than 6 mm.

The height H of the defect is calculated according to the following equation (4).

$$H = 0.94X \cdot 10^{\frac{h-39}{20}} \qquad (4)$$

(ii) When the plate to be inspected has a thickness of larger than 6 mm.

Figure 17A:
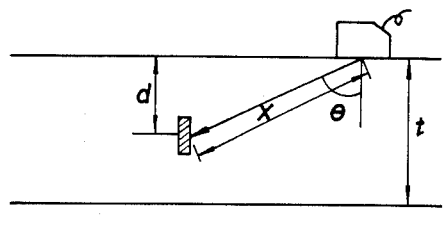
Figure 17B:
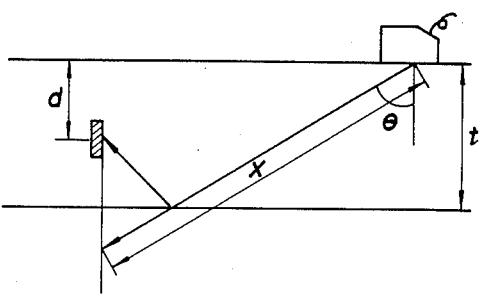

(a) The depth d of the defect is found according to equation (5) or (6) as shown in FIGS. 17(A), 17(B), i.e., $$d = X \cos \theta \qquad (5)$$

$$d = 2t - X \cos \theta \qquad (6)$$

In the equations (5) and (6), t denotes a plate thickness (mm), and $\theta$ denotes an incident angle determined by the probe, which can be input by the operator using keys. Here, the equation (5) holds when $d \leq t$, and the equation (6) holds when $d = t$. In this apparatus, furthermore, the depth d of the defect is found according to the equation (5) and is compared with the thickness t. When $d > t$, the calculation is performed again according to the equation (6).

When the result of calculation is $d \leq 3$, the defect is displayed to exist on the surface. When $d > 3$, the defect is displayed to exist in an internal portion.

(b) As a result of operation of (a) above, when $d \leq 3$, (surface defect), the height H of the defect is measured according to the following equation (7) and when $d > 3$ (internal defect) and $6 < t \leq 28$, the height H of the defect is measured according to the following equation (8) (the above are the cases of automatic mode).

When the surface defect or the internal defect can be discriminated by the operator, however, discrimination by the calculated result of (a) above can be changed by the key input. In the case of the surface defect, the height of the defect is found according to the equation (7). In the case of the internal defect, the height of the defect is found according to the equation (8).

$$H = 0.94X \cdot 10^{\frac{h-39}{19.2}} \qquad (7)$$

$$H = 0.94X \cdot 10^{\frac{h-40}{26}} \qquad (8)$$

(C-3) Measuring function by the surface-wave method of mode conversion.

The surface-wave method of mode conversion finds the size of defect by utilizing the difference of beam distance between the echo of a transversal wave directly reflected from the defect and the echo which is obtained based upon the mode conversion of the transversal wave into the surface wave at the defect (see "Non-destructive Inspection", Vol. 28, No. 3, 1979).

Figure 18:
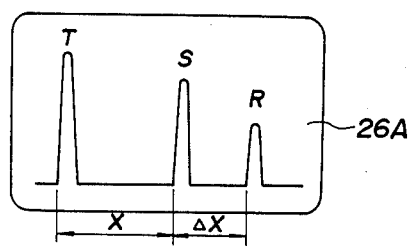

When the material to be inspected has a plate thickness of greater than 28 mm, the internal defect is measured relying upon this system. According to this system as shown in FIGS. 14 and 18, the height H of the defect is calculated relying upon a time difference $\Delta X$ between the echo (S echo) of the transversal wave of the directly reflected wave and the echo (R echo) obtained based upon the mode conversion of from the transversal wave into the surface wave at the defect. Here, as will be obvious from FIGS. 14(A), 14(B) and 14(C), the internal defect may assume the form of a plane or a spherical shape. Here, the shape should be discriminated by the operator.

In this system, the arithmetic operation is carried out according to the following procedure.

(i) The depth d of the defect is calculated according to the equations (5), (6). In this case, however, the beam path X is that of the S echo. The order of calculation is the same as that of (C-2)-(ii)-(a). As a result of calculation, when $d \leq 3$, the surface defect is indicated and when $d > 3$, the internal defect is indicated.

(ii) As a result of calculation of (i) above, when $d \leq 3$ (surface defect), the calculation is carried out using the equation (7).

(iii) As a result of calculation of (i) above, when $d > 3$ (internal defect), either the spherical defect or planar defect is designated to calculate the height of the defect according to the following equation (9) or (10).

(a) In the case of the planar defect:

$$H = 0.91 \Delta X \qquad (9)$$

(b) In the case of the spherical defect:

$$H = 0.58 \Delta X \qquad (10)$$

(iv) In (ii) above, when the operator can discriminate the surface defect or the internal defect beforehand, the calculated result of (i) can be changed by the key input. In the case of a surface defect, the height of the defect is calculated according to the equation (7). In the case of an internal defect, the height of the defect is calculated using the equation (9) or (10) in compliance with the procedure of (iii).

(C-4) Measuring function by the 6-dB drop method.

In scanning the probe in the back and forth directions, there exists a proportional relationship between the amount of movement in the back and forth directions and the size of defect at the time when the echo height drops by 6-dB (i.e., $\frac{1}{2}$) from a maximum echo height. The 6-dB drop method is to find the size of defect by utilizing this relationship (see Material puf-/e,uml/u/ ng, Vol. 10, No. 10, p. 329, 1968).

According to this method, the probe is manipulated to find the height of the defect from the range of movement of the probe at the time when the height of echo drops by 6-dB from the maximum height of the echo. There exist two cases as shown in FIGS. 19(A) and 19(B).

Figure 19A:
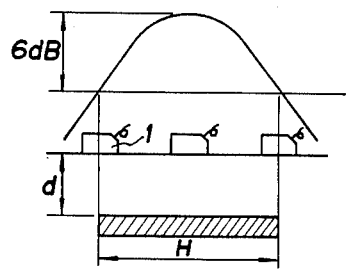
Figure 19B:
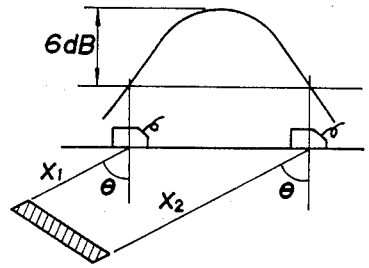

Namely, FIG. 19(A) is the case of vertical flaw detection, and FIG. 19(B) is the case of angle beam flaw detection.

(i) In the case of vertical flaw detection.

The height H of the defect is found from the moving amount of probe as shown in FIG. 19(A). In this case, the depth d of the defect is $d = X$ (X: beam path).

(ii) In the case of tilted-angle flaw detection.

The height H of the defect is found from the following equation (11).

$$H = (X_2 - X_1) \cos \theta \qquad (11)$$

In this case, the depth of the defect is found from the equation (5) or (6) by using the beam path X at the time when the echo height becomes maximum. Here, $X_1$ denotes a beam path at a probe position where the echo height drops by 6-dB from the maximum echo height in the forward direction, and $X_2$ denotes a beam path in the backward direction. In this system, furthermore, the alarm level may be set at a point which is lower than the maximum echo height by 6-dB, so that the alarm is produced and the lamp turns on when the level drops by 6-dB from the maximum echo height. At this moment, the operator inputs the height of the echo.

(C-5) Measuring function by the method of scattered longitudinal waves.

According to the method of scattered longitudinal waves, the size of the defect is found from the difference of beam path of echoes by utilizing the scattered echoes from the upper and lower ends of the defect, that are obtained when the longitudinal waves are permitted to be incident nearly in parallel with respect to the plane of the defect (see "HITACHI HYORON", Vol. 64, No. 9, p. 69, 1982).

Figure 20A:
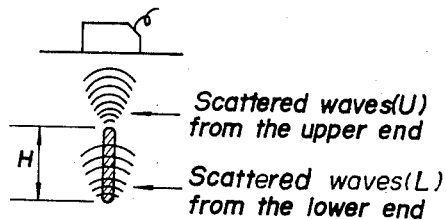
Figure 20B:
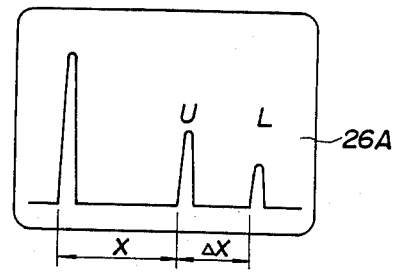

As shown in FIGS. 20(A) and 20(B), this system finds the height of the defect from the time difference $\Delta X$ between the scattered waves U from the upper end and the scattered waves L from the lower end when the longitudinal waves are permitted to be incident. The height H of the defect is given by the following equation (12).

$$H = \Delta X \quad (12)$$

The depth d of the defect is given by the following equation (13).

$$d = X + \frac{\Delta X}{2} \quad (13)$$

(C-6) Measuring function by the method of peak echo at an end portion.

According to the method of peak echo at an end portion, a transversal wave is permitted to be incident upon the planar defect, whereby an echo is obtained from an end portion of the defect. Namely, the size of defect is found from a beam path by which the echo is obtained (see "NON-DESTRUCTIVE INSPECTION", Vol. 26, No. 5, p. 320, 1977).

Figure 21A:
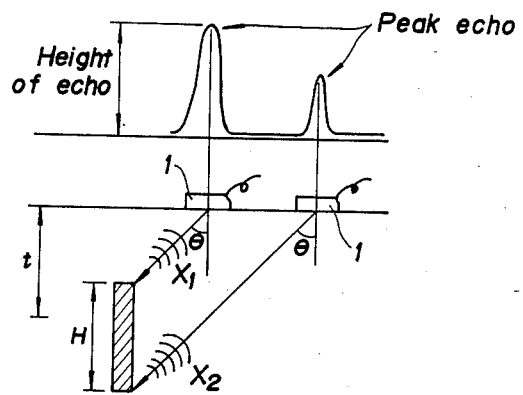
Figure 21B:
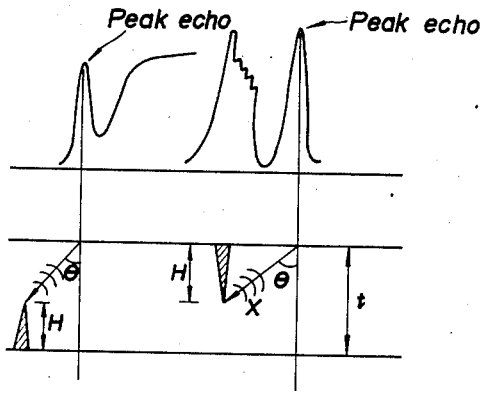

As will be obvious from FIG. 21, the object to be measured may be the internal defect (diagram (A)) or the opening defect in the surface (diagram (B)). First, the depth d of the defect is found from the equation (5) or (6), and the operator discriminates which equation should be used from among the equations (14), (16) and (17), to calculate the height H of the defect. When the result of the calculation by the equation (5) or (6) turns out to be the surface defect, the height H of the defect only should be calculated. In the case of an internal defect, the height H of the defect should be found, and the depth d of the defect should be calculated again.

(i) In the case of an internal defect.

Find the height H of the defect according to the following equation (14).

$$H = (X_2 - X_1) \cos \theta \quad (14)$$

Here, $X_1$ denotes a beam distance of when a peak echo is obtained in the forward direction, and $X_2$ denotes a beam distance in the backward direction.

The depth d of the defect is found from the following equation (15).

$$d = X_1 + \frac{H}{2} \cos \theta \quad (15)$$

(ii) In the case of an opening defect in the surface.

When the opening defect in the surface exists on the same plane as that of the detected flaw, the height H of the defect is found from the following equation (16).

$$H = X \cos \theta \quad (16)$$

When the opening defect in the surface exists on the plane opposite to that of the detected flaw, the height H of the defect is found from the following equation (17).

$$H = t - X \cos \theta \quad (17)$$

Where t denotes a plate thickness of a material to be inspected.

(C-7) Other functions.

(i) Rejection function.

The rejection function works to remove miscellaneous echoes that are unnecessary for the flaw detection. When the rejection function is being effected, a rejection lamp on the front panel turns on to draw attention for recording the data.

(ii) Function for switching waveform.

The shape of the waveform displayed can be selected to obtain a waveform depending upon the measurement and the object of display.

(iii) Function for searching desired echo.

A function to find the S echo and R echo that will be used for the surface-wave method of mode conversion. Usually, waveforms displayed on the cathode-ray tube are so complex that the operator can find a desired echo only with great difficulty unless he is accustomed to it. With this function, if the desired S echo and R echo as well as a possible waveform are designated (using the touch panel), beam paths of the two waves are stored. The echo positions are then moved, and the operator again designates the above-mentioned two waves (using the touch panel). The microcomputer automatically performs the calculation, and displays that the solution is correct (i.e., the designated two waves are the S echo and the R echo) when the difference is smaller than 10% between the previous beam paths and the beam paths of this time. The apparatus, further has two rechecking functions.

(a) Clear function.

When it is desired to check again the calculation that has been once performed by the above-mentioned system, the clear function should be put into effect. Then, the display of correct solution disappears, and the S echo and R echo can be searched again. The method of operation and the standard of judgement are the same as those of the first time.

(b) Function to check three times.

This apparatus effects the checking twice. When it is discriminated that the solution is correct, the checking can be effected once again to re-confirm the result. In this case, the average value of the data of the first and second times is compared with the data of the third time, and the correct solution is displayed when the deviation is smaller than 10% therebetween.

When the above-mentioned two functions are to be used, an average value of beam paths at the time of checking should be used as a beam path X.

Figure 22:
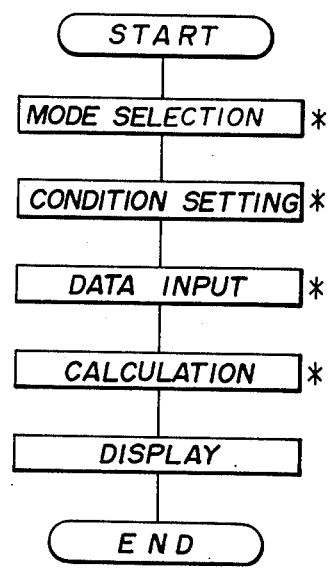
FIGS. 22 and 23 are flow charts for explaining the processing.
Figure 23:
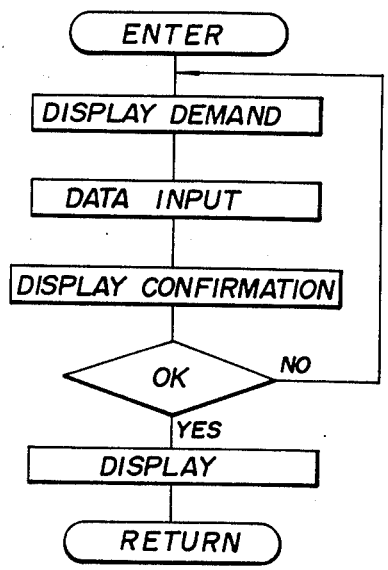

FIGS. 22 and 23 are flowcharts illustrating the processing by the microcomputer. The flowchart of FIG. 22 shows the flow of the whole operation. This flowchart is stored in the memory as a program in the microcomputer. The program of FIG. 22 is started when the power source is turned on, and a reset signal is applied thereto.

In the step of "mode selection", which operation mode should be used is determined by the operator among the "measurement of surface pressure", "flaw detection", "calibration", and "test". When the "flaw detection" is selected, the operator further designates which measuring method should be employed from among six measuring methods.

In the step of "condition setting", there are set various measuring conditions such as angle of refraction of the probe that is used, and plate thickness and shape of the material that is to be inspected.

The step of "data input" is a practical measuring portion which introduces data from the touch panel.

The step of "calculation" calculates the data introduced in the step of "data input" from the touch panel, relying upon a predetermined equation determined by the item of measurement and method, and finds the measured result.

The step of "display" displays the calculated result in terms of numerical values on the liquid crystal display unit.

To reduce the burden on the operator, furthermore, the apparatus of this embodiment has a man-machine interface function based upon the liquid crystal display unit.

In general, though not only limited to the measuring instruments, as the functions become sophisticated and diversified, people find it difficult to use the equipment unless they become well versed in its handling operation. Or, an increased burden is placed on the operator who must comprehend all of the equipment to fully draw its functions.

According to this embodiment, therefore, the procedure for operation and the contents of operation are displayed successively on the liquid crystal display unit, so that the operator can operate according to the displayed contents to take measurements.

FIG. 23 is a flowchart of the man-machine interface therefor. The program of flowchart of FIG. 23 is performed on a subroutine basis, and is started by the main program every time when the man-machine interface is needed in the steps marked with * in the flowchart of FIG. 22. In the step of "display demand" in the flowchart of FIG. 23, the content that should be done next by the operator is displayed on the liquid crystal display unit.

The step of "data input" reads the data designated by the operator through keys or reads the data of measurement sent from the touch panel.

In the step of "display confirmation", the data designated by the operator through keys or the data sent from the touch panel, are displayed on the liquid crystal display unit to ask the operator whether there is any incorrect instruction.

In the step of "OK (judgement)", the operator confirms the above-mentioned display and inputs either OK or NO. When OK is input, the program proceeds to the step of "display". When NO is input, the program returns to the step of "display demand", so that the data can be input again.

In the step of "display", the data designated by the operator is displayed on the liquid crystal display unit.

With the above-mentioned system, the operator needs read the instruction manual once to roughly know how to operate the apparatus. In other words, without having to know the details, the operator is allowed to carry out the operation sufficiently. Therefore, reduced burden is placed on the operator, and erroneous operation can be eliminated.

Figure 24:
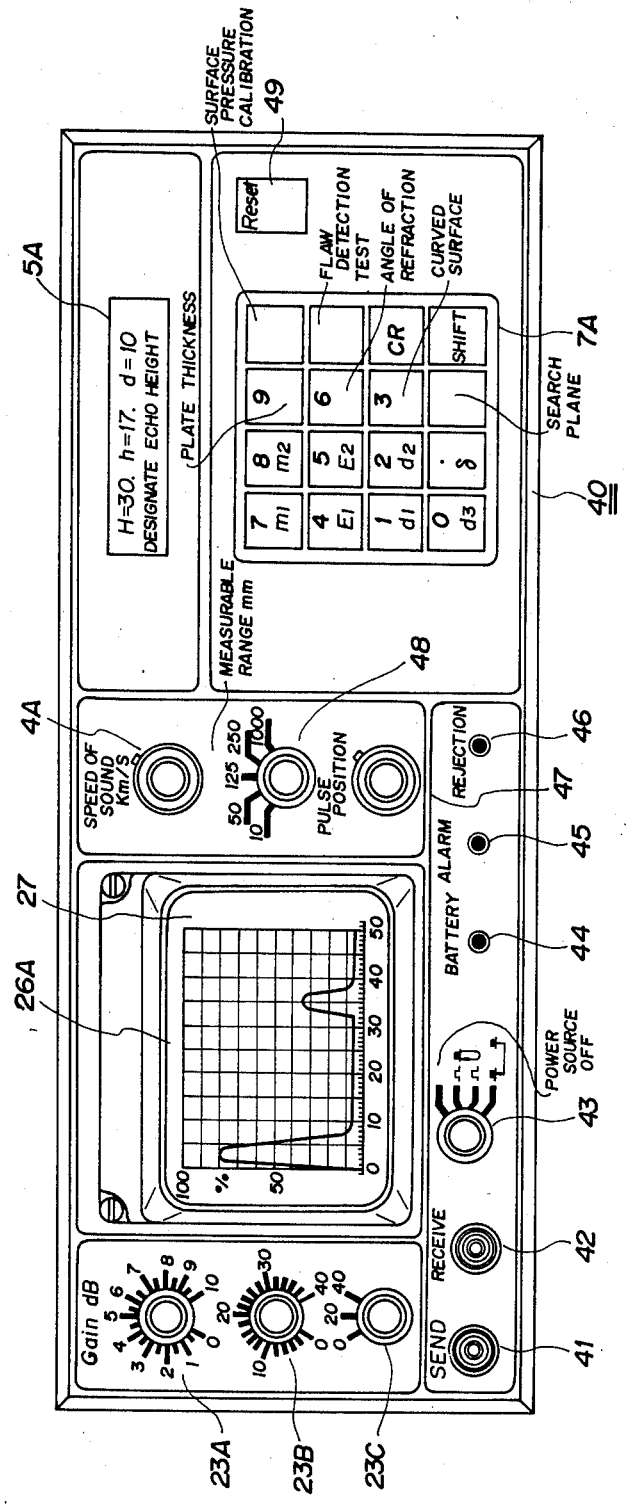
FIG. 24 is a diagram of the front panel.

FIG. 24 shows the arrangement of various switches and keys on the front panel 40 when the embodiment is practically realized in the form of a composite measuring apparatus. The front panel 40 has a display surface 26A of CRT, a display surface 5A of liquid display unit 5, keyboard surface 7A, setting switches 23A, 23B and 23C of logarithm converter 23, and a setting switch 4A of repetitive period setter 4. The apparatus further has a measurable range setter 48, a terminal 41 for sending signals to the probe 1, a terminal 42 for receiving signals from the probe 1, a power-source application indication portion 43, a lamp 44 for battery, an alarm lamp 45, a lamp 46 for rejection, a switch 47 for designating pulse position, and a reset button 49, that are not shown in the embodiment of FIG. 1.

The front panel 40 may measure 10 cm high, 20 cm wide, 30 cm deep, and may weight about 5 kg, featuring very small size. Therefore, the apparatus can be easily transported to various measuring sites, and can be adapted for measuring various objects.

This embodiment gives the effects as described below.

(1) Not only the depth of defect, but also the size and shape of defect can be measured, enabling the apparatus to find wide applications.

(2) Any point on the cathode-ray tube can be designated (depressed or touched) to read and calculate the data of wave form at that point.

(3) The pressure of contacting surfaces such as of bearings can be measured, making it easy to inspect and check construction machinery and structures.

(4) The setting work and operation are facilitated by using a microcomputer. Further, the size of defect and pressure of contacting surfaces are digitally displayed.

(5) Being powered by a storage battery, the apparatus can be conveniently used in the site.

In the mode of flaw detection, there also exist other measuring modes in addition to the aforementioned six modes. For instance, a widely-known DGS (distance gain size) method or an F/B (flaw/bottom) method may be adapted.

The present invention can further be adapted to a variety of observation signals in addition to ultrasonic flaw detection. When a material is vibrated using a vibrator, the material being vibrated exhibits waveforms similar to those responding to ultrasonic waves. Therefore, the present invention can be adapted to observing such vibration waveform.

Figure 25:
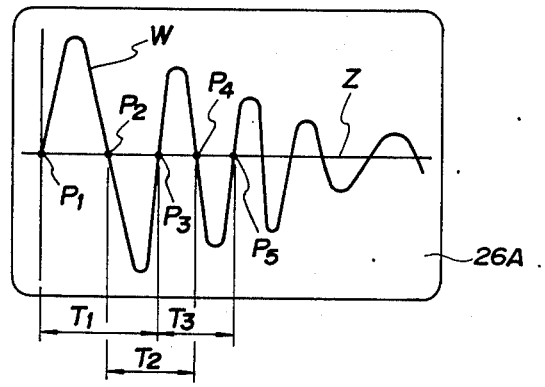
FIG. 25 is a diagram showing the detection of frequency.

FIG. 25 is a diagram where observation signals for measuring the frequency are introduced and are displayed as an observation waveform on the display surface 26A of the CRT. The observation waveform W is attenuating as a whole, and a section of each period is detected from this waveform. For this purpose, crossing points $P_1$, $P_2$, $P_3$, $P_4$ and $P_5$ on the zero level Z are found. The microcomputer 10 introduces crossing points on the zero level, converts the coordinate system on the position detecting panel into the coordinate system on the picture plane of CRT, and finds the periods $T_1$, $T_2$, $T_3$. Using these values $T_1$, $T_2$, $T_3$, the frequency f is found by, for instance, the averaging method, to obtain, $$T = \frac{1}{3}\left(\frac{1}{T_1} + \frac{1}{T_2} + \frac{1}{T_3}\right)$$

According to the present invention described in the foregoing, a position detecting panel is mounted on the display surface of an oscilloscope, and an indicated position is sent to the microcomputer from the position detecting panel. Therefore, measurement can be easily taken automatically by utilizing know-how of measurement that is obtained empirically. Furthermore, since the position is designated using the position-detecting panel, the computer needs have a memory of a small capacity. Further, a considerable number of boards are not required, and there is provided a numerically measuring apparatus which is compact as a whole and is light in weight.

What is claimed is:

1. A man-machine interface type portable ultrasonic composite measuring apparatus comprising:
   a keyboard device for designating a certain mode from among a plurality of ultrasonic composite measuring modes;
   a microcomputer having a plurality of processing programs respectively corresponding to said plurality of composite measuring modes, and which reads one of said processing modes which corresponds to said mode designated by the keyboard device, and which processes specified information consisting of a measurement procedure, a measurement object and a measurement position, in accordance with the read-out processing program, and which takes in external measured information to be stored as measurement data;
   a display unit for displaying said measurement procedure, said measurement object and said measurement position obtained during said processing by said microcomputer;
   an oscilloscope device for directly displaying in real-time responsive observation wave signals relating to an object to be inspected, obtained in accordance with the displayed content in said display unit, from an ultrasonic probe, without storing them;
   a transparent position-detecting panel which is mounted on a display surface of said oscilloscope device and which inputs coordinate signals of designated points on said responsive observation signal waveform displayed on said display surface;
   and an A-D converter for converting coordinate signals inputted from said panel into digital signals and for sending said converted coordinate signals to the microcomputer as measurement information.

* * * * *